(12) United States Patent
Hendrick et al.

(10) Patent No.: US 10,820,942 B2
(45) Date of Patent: Nov. 3, 2020

(54) INTERNAL RAIL SYSTEM FOR LASER CATHETER

(71) Applicant: The Spectranetics Corporation, Colorado Springs, CO (US)

(72) Inventors: Brandon Thomas Hendrick, Colorado Springs, CO (US); Ali Hartley, Colorado Springs, CO (US); Grant Donnelly Foy, Colorado Springs, CO (US)

(73) Assignee: THE SPECTRANETICS CORPORATION, Colorado Springs, CO (US)

( * ) Notice: Subject to any disclaimer, the term of this patent is extended or adjusted under 35 U.S.C. 154(b) by 282 days.

(21) Appl. No.: 15/858,561

(22) Filed: Dec. 29, 2017

(65) Prior Publication Data
US 2018/0185095 A1 Jul. 5, 2018

Related U.S. Application Data

(60) Provisional application No. 62/440,257, filed on Dec. 29, 2016.

(51) Int. Cl.
*A61B 18/24* (2006.01)
*A61B 18/14* (2006.01)
*A61B 17/00* (2006.01)
*A61B 18/00* (2006.01)
*A61B 17/22* (2006.01)

(52) U.S. Cl.
CPC ........ *A61B 18/245* (2013.01); *A61B 18/1492* (2013.01); *A61B 2017/003* (2013.01); *A61B 2017/00867* (2013.01); *A61B 2017/22038* (2013.01); *A61B 2018/00351* (2013.01); *A61B 2018/00577* (2013.01)

(58) Field of Classification Search
CPC .............. A61B 18/245; A61B 18/1492; A61B 2017/00867; A61B 2018/00577; A61B 2017/22038; A61B 2018/00351; A61B 2017/003
See application file for complete search history.

(56) References Cited

U.S. PATENT DOCUMENTS 5,026,366 A * 6/1991 Leckrone ............... A61B 18/20
606/15
2002/0103459 A1 * 8/2002 Sparks ............... A61B 17/3207
604/164.13

(Continued)

*Primary Examiner* — Gary Jackson
*Assistant Examiner* — Sebastian X Lukjan

(57) ABSTRACT

Embodiments include a catheter system comprising an elongated housing having a housing channel disposed between a first proximal end and a first distal end. The first distal end includes a ramp, having an inclining proximal section and an apex section, and a nose section. The catheter system further includes a rail wire channel in communication with the ramp but not the nose section and a laser delivery member being at least partially disposed within the housing channel and movable therein. In some embodiments, the catheter system includes a rail wire fixedly attached to and terminating at the first distal end of the elongated housing, wherein the rail wire extends through the rail wire channel, and wherein the laser delivery member is slidably coupled to the rail wire.

18 Claims, 17 Drawing Sheets

(56) References Cited

U.S. PATENT DOCUMENTS

| | | | |
|---|---|---|---|
| 2003/0171741 A1* | 9/2003 | Ziebol | A61B 18/245 606/7 |
| 2008/0097298 A1* | 4/2008 | Fisher | A61B 17/320758 604/103.04 |
| 2008/0097299 A1* | 4/2008 | Andreas | A61F 2/958 604/103.04 |
| 2010/0114066 A1* | 5/2010 | Makower | A61B 5/06 604/514 |

* cited by examiner

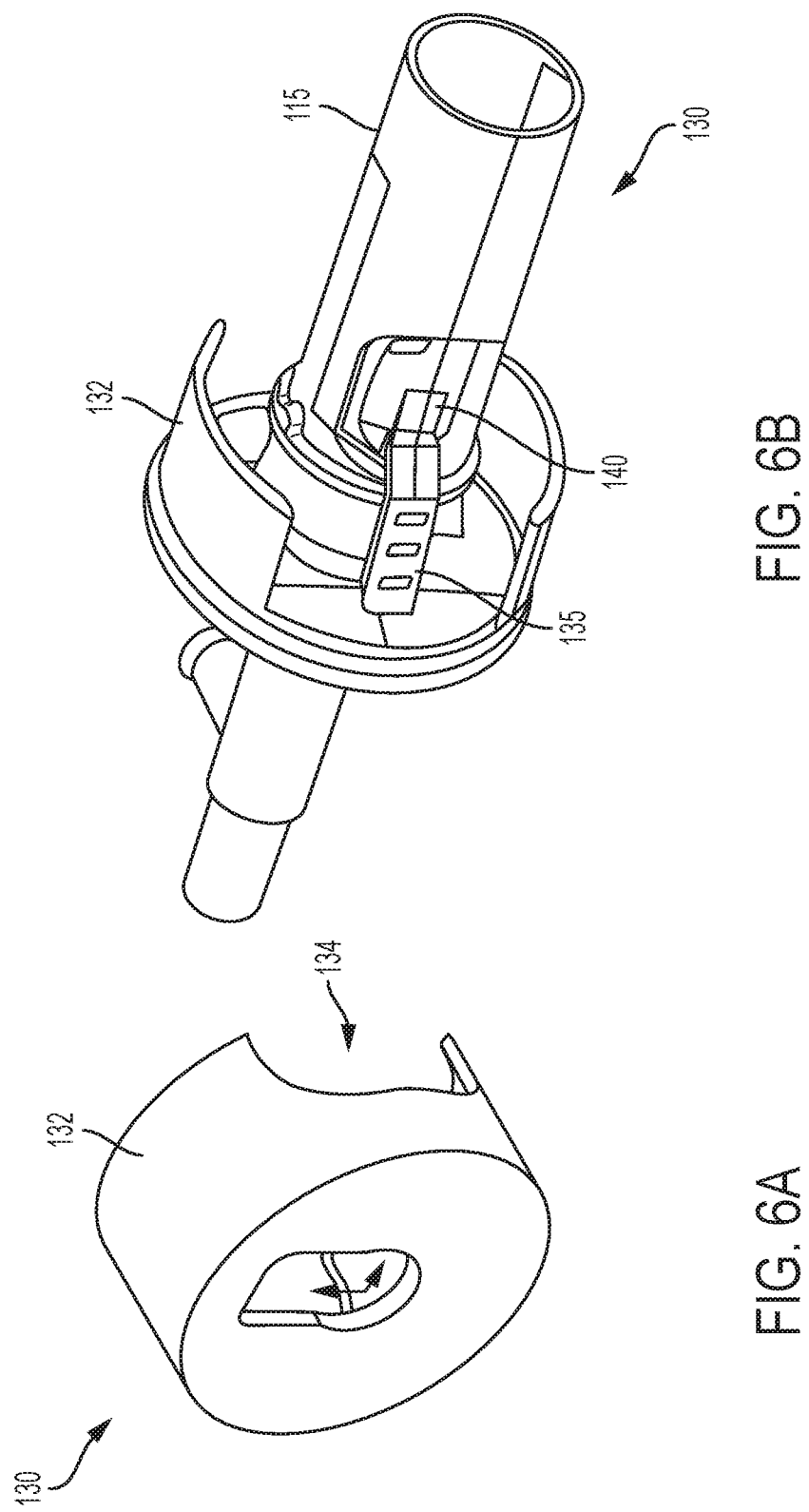

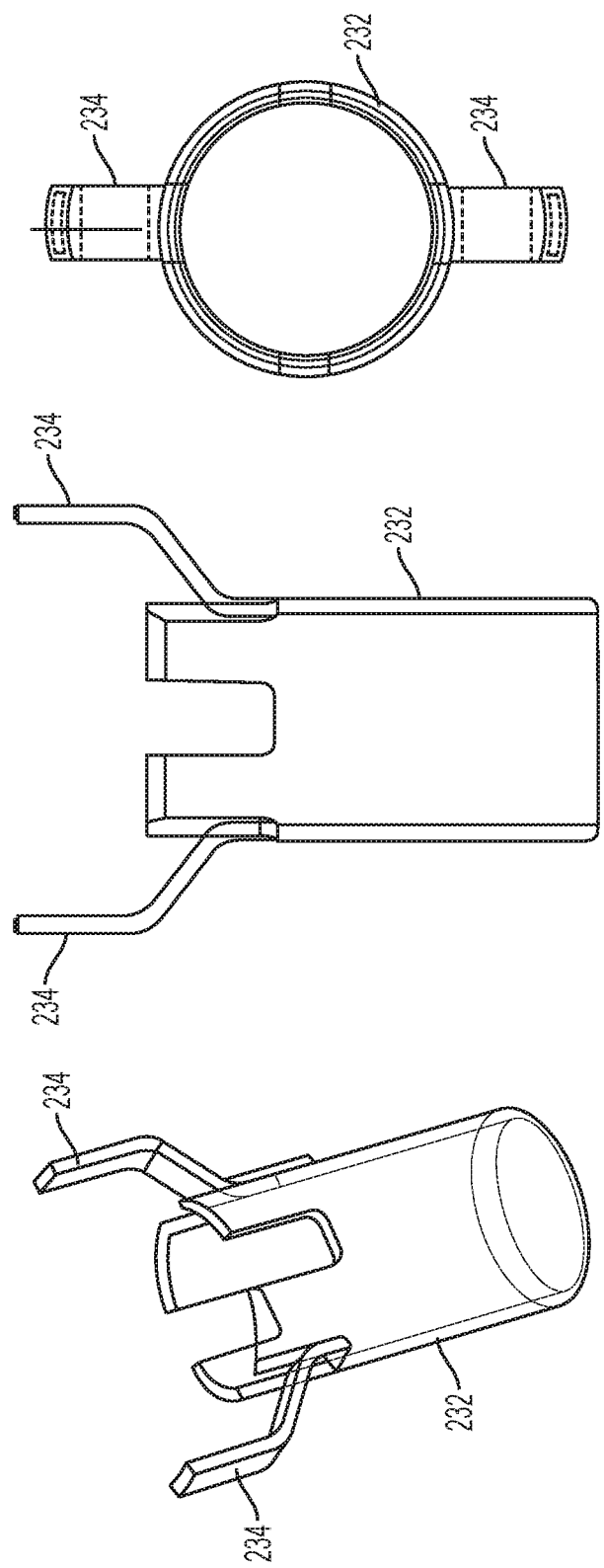

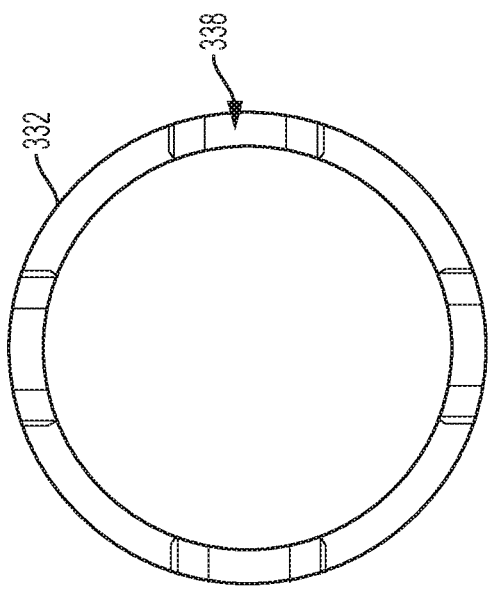
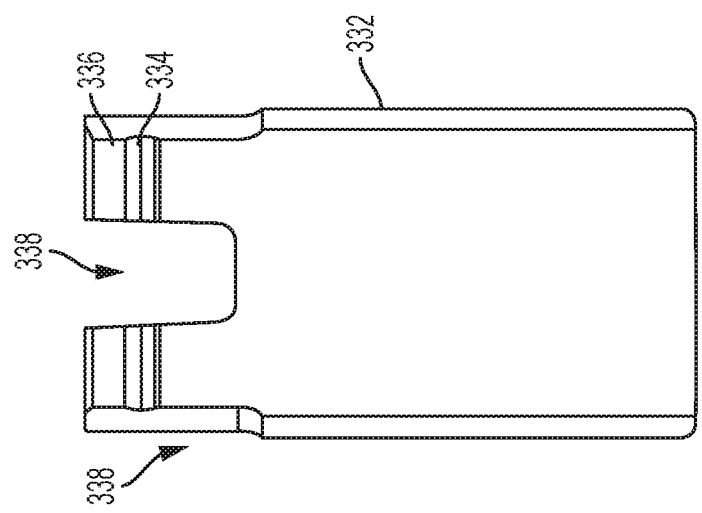
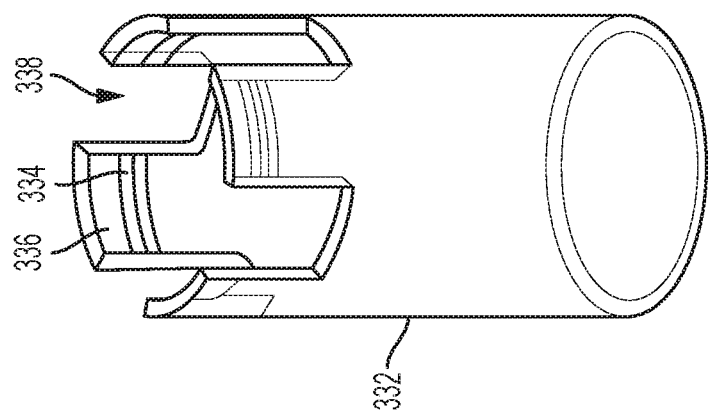
FIG. 8C
FIG. 8B
FIG. 8A

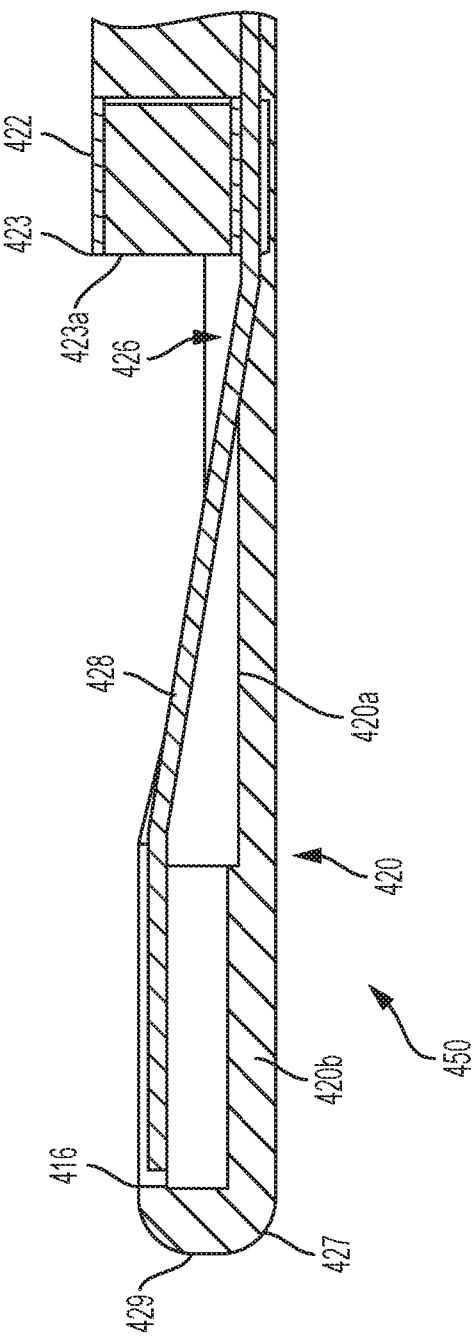
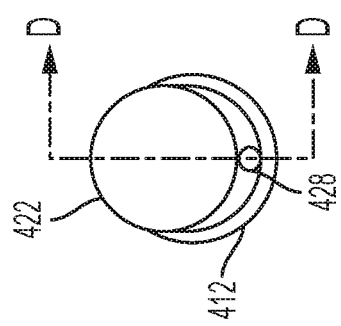
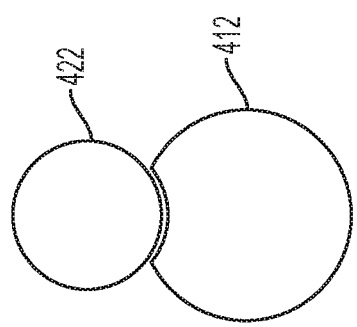

INTERNAL RAIL SYSTEM FOR LASER CATHETER

CROSS-REFERENCE TO RELATED APPLICATION

The present application claims the benefit of and priority to, under 35 U.S.C. § 119(e), U.S. Provisional Application Ser. No. 62/440,257, filed Dec. 29, 2016, entitled INTERNAL RAIL SYSTEM FOR LASER CATHETER, which is hereby incorporated by reference in its entirety for all purposes.

TECHNICAL FIELD

The embodiments described herein are generally directed to an apparatus and methods for the delivery of laser energy, including without limitation, to a laser delivery catheter.

BACKGROUND

Arteries are the primary blood vessels that are responsible for providing blood and oxygen to the heart muscle. Arterial disease occurs when arteries become narrowed or blocked by a buildup of plaque (as some examples, atherosclerotic plaque or other deposits). When the blockage is severe, the flow of blood and oxygen to the heart muscle is reduced, causing chest pain. Arterial blockage by clots formed in a human body may be relieved in a number of traditional ways. Drug therapy, including nitrates, beta-blockers, and peripheral vasodilatator drugs to dilate the arteries or thrombolytic drugs to dissolve the clot, can be effective. If drug treatment fails, angioplasty may be used to reform or remove the atherosclerotic plaque or other deposits in the artery.

Traditional balloon angioplasty is sometimes used to address the blockage by inserting a narrow, flexible tube having a balloon into an artery in the arm or leg. The blocked area in the artery can be stretched apart by passing the balloon to the desired treatment site and gently inflating it a certain degree. In the event drug therapy is ineffective or angioplasty is too risky (introduction of a balloon in an occluded artery can cause portions of the atherosclerotic material to become dislodged and may cause a total blockage at a point downstream of the subject occlusion thereby requiring emergency procedures), a procedure known as laser ablation may be indicated.

Laser ablation therapy includes inserting a laser catheter into an artery in the arm or leg or other entry point created in the body. The laser catheter contains one or more optical fibers, which transmit laser energy. The laser catheter is then advanced inside the artery to the targeted obstruction at the desired treatment site. After the laser catheter has been positioned, the laser is energized to "remove" the obstruction via ablation of the obstruction. In many procedures, the lesion is often engaged similar to conventional balloon angioplasty by crossing the blockage with a guidewire. The laser catheter's thin, flexible optical fibers facilitate the desired positioning and alignment of the catheter. Using the excimer laser, the clinician performs a controlled blockage removal by sending bursts of ultraviolet light through the catheter and against the blockage, a process called "ablation." The catheter is then slowly advanced through the blockage reopening and/or enlarging the lumen through the artery. If there are multiple blockages, the catheter is advanced to the next blockage site and the above step is repeated. When the blockage(s) appear(s) to be cleared, the catheter is withdrawn.

However, due to the configuration of the optical fibers in most prior art laser catheters, the clinician is able to ablate only material that is typically directly in front of the distal end of the catheter. Thus, the debulked tissue area is limited to an area approximately the area of the optical fiber(s) area at the distal end of the catheter.

Thus, it would be desirable to provide an apparatus and methods that could bias the distal end of the laser catheter in a desired direction to enable the clinician to ablate an area larger than the area of the distal end of the catheter where the distal end(s) of the optical fiber(s) are exposed.

BRIEF SUMMARY

These and other needs are addressed by the various aspects, embodiments, and configurations of the present disclosure.

Embodiments of the present disclosure include a catheter comprising: an elongated housing having a first proximal end and a first distal end, the elongated housing having a lumen disposed between the first proximal end and the first distal end, the lumen having an opening at the first distal end; a laser delivery member having a second proximal end and a second distal end, the laser delivery member being at least partially disposed within the lumen and movable therein; and a handle associated with the first proximal end and having an actuation mechanism coupled to the laser delivery member. In some embodiments, the actuation mechanism comprises: a body including a distal disc and at least one release arm, the distal disc including a rotatable cylindrical sleeve extending proximally therefrom and having at least one window; and a plunger including a proximal disc, the plunger disposed at least partially within the body. In some embodiments, distally advancing the plunger includes depressing the proximal disc and the distal disc to advance the laser delivery member; whereupon: in a first rotatable position, the at least one window is offset relative to the at least one release arm; the release arm configured to being protected to prevent being depressed; and in a second rotatable position, the at least one window is aligned relative to the at least one release arm, the release arm configured to being depressed to retract the laser delivery member.

The catheter, wherein the actuation mechanism further comprises a spring disposed within the body.

The catheter, wherein the at least one release arm further includes at least one detent wherein the at least one detent is engageable with an internal body feature to compress the spring in the first rotatable position.

The catheter, wherein the rotatable cylindrical sleeve is configured to cover but not contact the at least one release arm in the first rotatable position.

Embodiments of the present disclosure include a catheter comprising: an elongated housing having a first proximal end and a first distal end, the elongated housing having a lumen disposed between the first proximal end and the first distal end, the lumen having an opening at the first distal end; a laser delivery member having a second proximal end and a second distal end, the laser delivery member being at least partially disposed within the lumen and movable therein; and a handle associated with the first proximal end and having an actuation mechanism coupled to the laser delivery member. In some embodiments, the actuation mechanism comprises: a body including a distal disc and at least one release arm; and a plunger including a proximal disc, the plunger disposed at least partially within the body. In some embodiments, distally advancing the plunger includes depressing the proximal disc and the distal disc to advance the laser delivery member; and a moveable sleeve disposed about the body and including at least one protector arm protruding distally therefrom; whereupon: in a first position, the at least one protector arm is aligned relative to the at least one release arm; the release arm configured to being protected to prevent being depressed; and in a second position, the at least one protector arm is offset relative to the at least one release arm, the release arm configured to being depressed to retract the laser delivery member.

The catheter, wherein the moveable sleeve is rotatable, slidable, or both.

The catheter, wherein the actuation mechanism further comprises a spring disposed within the body.

The catheter, wherein the at least one release arm further includes at least one detent wherein the at least one detent is engageable with an internal body feature to compress the spring in the first position.

The catheter, wherein the at least one protector arm is configured to cover but not contact the at least one release arm in the first position.

Embodiments of the present disclosure include a catheter comprising: an elongated housing having a first proximal end and a first distal end, the elongated housing having a lumen disposed between the first proximal end and the first distal end, the lumen having an opening at the first distal end; a laser delivery member having a second proximal end and a second distal end, the laser delivery member being at least partially disposed within the lumen and movable therein; and a handle associated with the first proximal end and having an actuation mechanism coupled to the laser delivery member. In some embodiments, the actuation mechanism comprises: a body including a distal disc and at least one release arm having at least one detent; and a plunger including a proximal disc, the plunger disposed at least partially within the body. In some embodiments, distally advancing the plunger includes depressing the proximal disc and the distal disc to advance the laser delivery member; and a slidable sleeve disposed about the body and including at least one internal circumferential groove; whereupon: in a first slidable position, an external surface of the at least one detent is in contact with the at least one internal circumferential groove; the at least one internal circumferential groove configured to restrict movement and to prevent the at least one release arm being depressed; and in a second slidable position, the external surface of the at least one detent is not in contact with the slidable sleeve, the release arm configured to being depressed to retract the laser delivery member.

The catheter, wherein the actuation mechanism further comprises a spring disposed within the body.

The catheter, wherein the at least one detent is engageable with an internal body feature to compress the spring in the first rotatable position.

The catheter, wherein the slidable sleeve further comprises windows.

Embodiments of the present disclosure include a catheter comprising: an elongated housing having a first proximal end and a first distal end, the elongated housing having a lumen disposed between the first proximal end and the first distal end, the lumen having an opening at the first distal end; a laser delivery member having a second proximal end and a second distal end, the laser delivery member being at least partially disposed within the lumen and movable therein; and a handle associated with the first proximal end and having an actuation mechanism coupled to the laser delivery member. In some embodiments, the actuation mechanism comprises: a body including a distal disc and at least one release arm; a plunger including a proximal disc, the plunger disposed at least partially within the body. In some embodiments, distally advancing the plunger includes depressing the proximal disc and the distal disc to advance the laser delivery member; and a moveable lock feature operatively connected to the body, whereupon: in a first position, the moveable lock feature is configured to prevent the at least one release arm being depressed to retain the laser delivery member in an advanced position; and in a second position, the moveable lock feature is configured to permit the at least one release arm being depressed to retract the laser delivery member to a retracted position.

The catheter, wherein the actuation mechanism further comprises a spring disposed within the body.

The catheter, wherein the at least one release arm further includes at least one detent wherein the at least one detent is engageable with an internal body feature to compress the spring in the first rotatable position.

The catheter, wherein the lock feature is configured to slide, rotate, or both to move from the first position to the second position.

The catheter, wherein the lock feature is a sleeve disposed circumferentially over the body.

The catheter, wherein the sleeve is restricts movement of the release arm or the detent in the first position.

The catheter, wherein the sleeve is a rotatable cylindrical sleeve configured to cover but not contact the at least one release arm in the first position.

Embodiments of the present disclosure include a catheter system comprising: an elongated housing having a first proximal end, a first distal end, a central axis, and a housing channel disposed between the first proximal end and the first distal end, a cavity disposed proximate the first distal end of the elongated housing and in communication with the housing channel. In some embodiments, the first distal end includes having: a ramp having an inclining proximal section and an apex section; a nose section; and a rail wire channel in communication with the ramp but not the nose section. In some embodiments, the catheter system further comprises a laser delivery member having a second proximal end, a second distal end, at least one optical fiber, the laser delivery member being at least partially disposed within the housing channel and movable therein, the ramp adapted to move the second distal end of the laser delivery member laterally away from the central axis of the elongated housing when the distal end of the laser delivery member is on the ramp; and a rail wire fixedly attached to and terminating at the first distal end of the elongated housing, wherein the rail wire extends through the rail wire channel, and wherein the laser delivery member is slidably coupled to the rail wire.

The catheter system, wherein the rail wire extends through the ramp but not the nose section.

The catheter system, wherein the nose section is a rounded tip having minimal thickness.

The catheter system, further comprising an actuation mechanism coupled to the elongated housing and the laser delivery member, the actuation mechanism having a body and a plunger disposed at least partially within the body, whereupon distally advancing the plunger advances the laser delivery member along the rail wire, the rail wire being adapted to position the second distal end laterally away from and generally parallel to the central axis as the second distal end is at or beyond the apex section of the ramp.

The catheter system, wherein the first distal end includes a first distal edge, the first distal edge defining a line extending therefrom and generally perpendicular to the central axis, and the second distal end includes a second distal edge, wherein distally advancing the plunger advances the second distal edge to the line.

The catheter system, the elongated housing further comprising a guidewire channel.

The catheter system, wherein the guidewire channel is in communication with the ramp.

The catheter system, further comprising a guidewire exiting through the guidewire channel.

The catheter system, wherein the guidewire channel includes a side port.

The catheter system, the elongated housing further comprising a sheath, wherein the guidewire channel is disposed within the sheath.

Embodiments of the present disclosure include a catheter system comprising: an elongated housing having a first proximal end, a first distal end, a central axis, and a housing channel disposed between the first proximal end and the first distal end, a cavity disposed proximate the first distal end of the elongated housing and in communication with the housing channel. In some embodiments, the first distal end includes having: a ramp having an inclining proximal section and an apex section; a nose section disposed distally of the ramp; and a rail wire channel in communication with the ramp. In some embodiments, the catheter system further comprises: a laser delivery member having a second proximal end, a second distal end, at least one optical fiber, and a guidewire channel, the laser delivery member being at least partially disposed within the housing channel and movable therein, the ramp adapted to move the second distal end of the laser delivery member laterally away from the central axis of the elongated housing when the distal end of the laser delivery member is on the ramp; a rail wire fixedly attached to and terminating at the first distal end of the elongated housing, wherein the rail wire extends through the rail wire channel, and wherein the laser delivery member is slidably coupled to the rail wire; and a guidewire extending through the guidewire channel and exiting the second distal end.

The catheter system, further comprising a trigger mechanism coupled to the elongated housing and the laser delivery member, the trigger mechanism having a body and a plunger disposed at least partially within the body, whereupon distally advancing the plunger advances the laser delivery member along the rail wire, the rail wire being adapted to position the second distal end laterally away from and generally parallel to the central axis as the second distal end is at or beyond the apex section of the ramp.

The catheter system, wherein the first distal end includes a first distal edge, the first distal edge defining a line extending therefrom and generally perpendicular to the central axis, and the second distal end includes a second distal edge, wherein distally advancing the plunger advances the second distal edge to the line.

The catheter system, wherein the rail wire and the guidewire do not enter or exit the nose section.

The catheter system, wherein the nose section is a rounded tip having minimal thickness.

Embodiments of the present disclosure include a method comprising: positioning a catheter system within a vessel, wherein the catheter system includes: an elongated housing having a first proximal end, a first distal end, a central axis, and a housing channel disposed between the first proximal end and the first distal end, a cavity disposed proximate the first distal end of the elongated housing and in communication with the housing channel. In some embodiments, the first distal end includes having: a ramp having an inclining proximal section and an apex section; a nose section disposed distally of the ramp; and a rail wire fixedly attached to and terminating at the ramp or nose section. In some embodiments, the catheter system further comprises: a laser delivery member having a second proximal end, a second distal end, at least one optical fiber, the laser delivery member being at least partially disposed within the housing channel and movable therein, the ramp adapted to move the second distal end of the laser delivery member laterally away from the central axis of the elongated housing when the distal end of the laser delivery member is on the ramp; and the rail wire extending through a rail wire channel and slidably connected to the laser delivery member. In some embodiments, the method further includes actuating the actuation mechanism, the actuation mechanism coupled to the elongated housing and the laser delivery member and including a body and a plunger disposed at least partially within the body, whereupon distally advancing the plunger advances the laser delivery member along the rail wire, the rail wire being adapted to position the second distal end laterally away from and generally parallel to the central axis as the second distal end is at or beyond the apex section of the ramp. In some embodiments, the method further includes activating a laser light source to generate light energy to ablate target material within the vessel.

The method further including the first distal end having a first distal edge, the first distal edge defining a line extending therefrom and generally perpendicular to the central axis, and the second distal end having a second distal edge, wherein distally advancing the plunger advances the second distal edge to the line.

The method, wherein the rail wire extends through the ramp but not the nose section.

The method, wherein the nose section is a rounded tip having minimal thickness.

The method, wherein positioning the catheter includes the laser delivery member being proximate to the target material, separated only by the minimal thickness of the rounded tip of the nose section.

As used herein, "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together. When each one of A, B, and C in the above expressions refers to an element, such as X, Y, and Z, or class of elements, such as $X_1$-$X_n$, $Y_1$-$Y_m$, and $Z_1$-$Z_o$, the phrase is intended to refer to a single element selected from X, Y, and Z, a combination of elements selected from the same class (e.g., $X_1$ and $X_2$) as well as a combination of elements selected from two or more classes (e.g., $Y_1$ and $Z_o$).

It is to be noted that the term "a" or "an" entity refers to one or more of that entity. As such, the terms "a" (or "an"), "one or more" and "at least one" can be used interchangeably herein. It is also to be noted that the terms "comprising", "including", and "having" can be used interchangeably.

A "catheter" is a tube that can be inserted into a body cavity, duct, lumen, or vessel, such as the vasculature system. In most uses, a catheter is a relatively thin, flexible tube ("soft" catheter), though in some uses, it may be a larger, solid-less flexible—but possibly still flexible—catheter ("hard" catheter).

A "coupler" or "fiber optic coupler" refers to the optical fiber device with one or more input fibers and one or several output fibers. Fiber couplers are commonly special optical fiber devices with one or more input fibers for distributing optical signals into two or more output fibers. Optical energy is passively split into multiple output signals (fibers), each containing light with properties identical to the original except for reduced amplitude. Fiber couplers have input and output configurations defined as M×N. M is the number of input ports (one or more). N is the number of output ports and is always equal to or greater than M. Fibers can be thermally tapered and fused so that their cores come into intimate contact. This can also be done with polarization-maintaining fibers, leading to polarization-maintaining couplers (PM couplers) or splitters. Some couplers use side-polished fibers, providing access to the fiber core. Couplers can also be made from bulk optics, for example in the form of microlenses and beam splitters, which can be coupled to fibers ("fiber pig-tailed").

An optical fiber (or laser active fibre) is a flexible, transparent fiber made of an optically transmissive material, such as glass (silica) or plastic, that functions as a waveguide, or "light pipe", to transmit light between the two ends of the fiber.

BRIEF DESCRIPTION OF THE DRAWINGS

The features and inventive aspects of the present disclosure will become more apparent upon reading the following detailed description, claims, and drawings, of which the following is a brief description.

FIG. 6A is a perspective view of a rotatable sleeve disc according to an example aspect of the present disclosure.

FIG. 6B is a perspective view of an actuation mechanism body and the rotatable sleeve disc shown in FIG. 6A.

FIG. 7A is a perspective view of an alternative sleeve having protector arms for an actuation mechanism according to an example aspect of the present disclosure.

FIG. 7B is a side view of the sleeve depicted in FIG. 7A.

FIG. 7C is a bottom view of the depicted in FIG. 7A.

FIG. 8A is a perspective view of a sleeve including an internal groove for impinging a detent of a release arm for an actuation mechanism according to an example aspect of the present disclosure.

FIG. 8B is a side view of the sleeve depicted in FIG. 8A.

FIG. 8C is a top view of the sleeve depicted in FIG. 8A.

FIG. 9C is a cross-sectional view of a laser delivery member relative to an elongated housing and a guidewire for a catheter system as shown inn FIG. 9B taken along cross section C-C.

FIG. 9D is a side cross-sectional view of a distal tip of a catheter including a nose section, a ramp, a rail wire, and a laser delivery member according to an example aspect of the present disclosure, the laser delivery member moveable relative to the rail wire and shown in a retracted position.

FIG. 9E is a cross-sectional view of a laser delivery member relative to an elongated housing and a guidewire for a catheter system as shown inn FIG. 9A taken from the distal end of the catheter system along line E-E.

DETAILED DESCRIPTION

Figure 1:
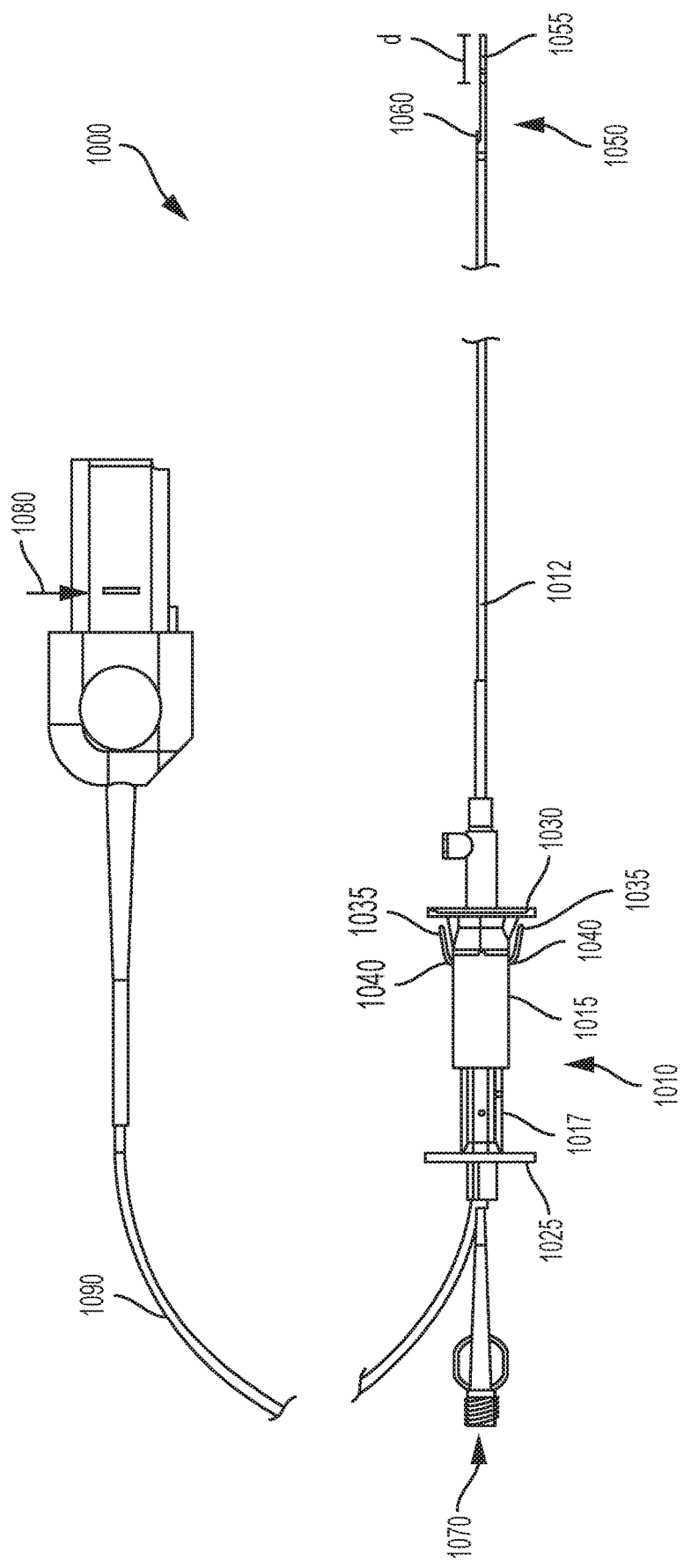
FIG. 1 is a perspective view of a prior art catheter system comprising a laser delivery member and an elongated housing.

Referring now to the drawings, illustrative embodiments are shown in detail. Although the drawings represent some embodiments, the drawings are not necessarily to scale and certain features may be exaggerated to better illustrate and explain an innovative aspect of an embodiment. Further, the embodiments described herein are not intended to be exhaustive or otherwise limit or restrict the embodiments of the present disclosure to the precise form and configuration shown in the drawings and disclosed in the following detailed description.

Referring now to FIGS. 1-4 showing a prior art catheter system 1000 that includes an elongated laser deliver member 1005, such as a laser catheter, coupled to and at least partially disposed within an elongated housing 1012. The laser delivery member 1005 and the elongated housing 1007 may be integral to one another or they may be separable from one another.

The elongated laser deliver member 1005 may include optical fibers (not shown), a coupler 1080 at its proximal end, laser emitters 1060, such as exposed ends of the optical fibers, at its distal end, and a flexible sheath 1090 encapsulating the optical fibers. The optical coupler 1080 connects the elongated laser deliver member 1005 to a laser system or laser generator that provides light energy to the optical fibers. An example of a laser system or generator is the CVX-300 Excimer Laser System, which is sold by The Spectranetics Corporation—the applicant of the present application.

The elongated housing 1007 may include a handle mechanism 1010 at its proximal end and a radial opening at, adjacent or toward its distal end portion 1050, and a flexible elongated hollow tube 1012 therebetween. The handle mechanism 1010 may have two portions that are moveable with respect to one another. For example, the handle mechanism 1010 may have a fixed portion, such as distal disc 1030, and a movable portion, such as proximal disc 1025. Alternatively, the fixed portion may be the proximal disc 1025, and the movable portion, may be the distal disc 1030. A further alternative is that both the proximal disc 1025 and the distal disc 1030 may be moveable.

Figure 2A:
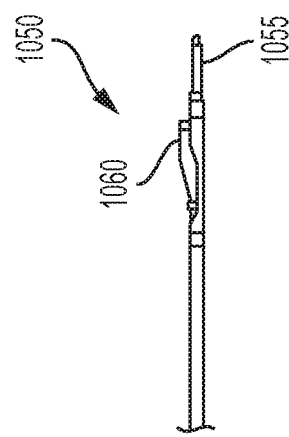
FIG. 2A is a perspective view of a prior art catheter system wherein a handle, which is attached to the elongated housing, is in an unactuated position, and the laser delivery member is in the retracted position with respect to the elongated housing.
Figure 2A:
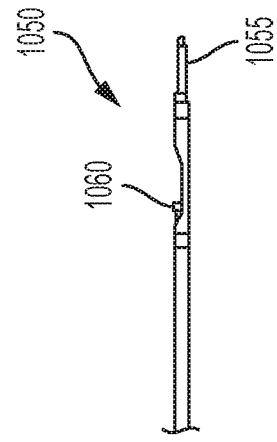
Figure 2A:
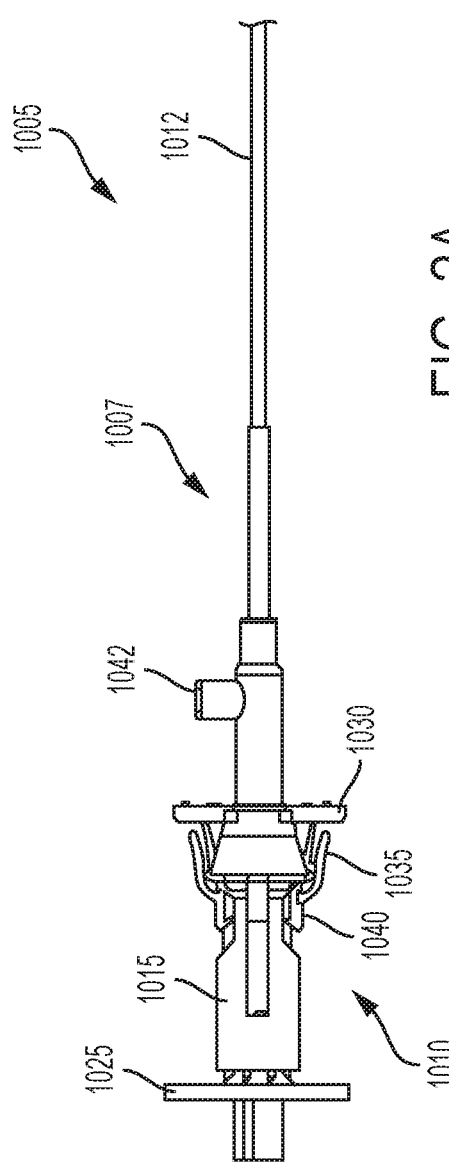
Figure 2B:
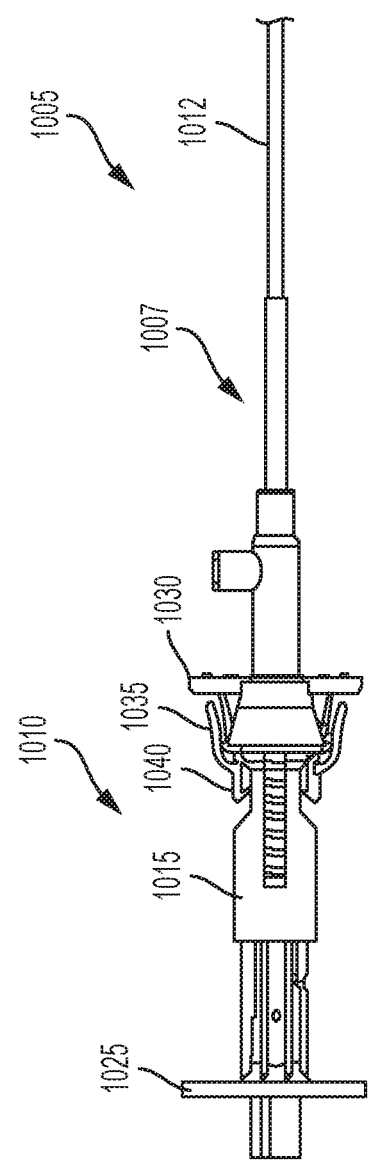
FIG. 2B is a perspective view of a prior art catheter system including wherein the handle is in an actuated position and the laser delivery member is in the extended position with respect to the elongated housing.

Assuming that the handle mechanism 1010 includes distal disc 1030 having a fixed portion and a proximal disc 1025 as the movable portion, as depicted in FIGS. 2A and 2B, the laser delivery mechanism 1005 is coupled to and fixed relative to the movable portion 1025 of the handle mechanism 1010 so that upon translation of the movable portion 1025, the distal end 1060 of the laser delivery mechanism 1005 translates within a lumen of the flexible sheath 1090 from a retracted position to an advanced position through the radial opening at the distal end of the elongated housing 1007. FIG. 2A illustrates catheter system 1000 wherein the proximal disc 1025 and the distal disc 1030 have been depressed and a spring (not shown) within body 1015 is tight or compressed, wherein detents 1040 of release arms 1035 engage with an internal body feature having grooves and/or ridges (not shown), thereby locking the laser delivery mechanism 1005, particularly the distal end 1060, in place (i.e., in an advanced position) relative to the distal disc 1030 of the handle mechanism 1010 and relative to the nosecone 1055 at the distal end of the elongated housing 1007. Release arms 1035 are also referred to as locking arms interchangeably herein. The detents 'click into' or engage with the internal body feature as the handle is compressed and the body feature compresses the spring. To release, the release arms are depressed and the detents pull out of the groves to release the force of the spring.

The laser delivery mechanism 1005 is held in the position, as shown in FIG. 2A, during ablation via the locking arms 1035 having detents 1040 engaged with the spring. Upon completion of ablation, the catheter system 1000 is removed from any target matter to be ablated by at least the distance or length of nosecone 1055. FIG. 2B illustrates laser delivery mechanism 1005 in the retracted position with respect to the elongated housing 1007, wherein detents 1040 of release arms 1035 are not engaged with the spring, and the spring within body 1015 is relaxed in an expanded configuration. During operation of the handle mechanism 1010, the locking arms 1035 may become disengaged with the detents 1040, thereby allowing laser delivery mechanism 1005 to move relative to the elongated housing 1007 during ablation. There is a long felt need to ensure that the handle actuation mechanism only actuates when depressed purposefully and not inadvertently.

Figure 3:
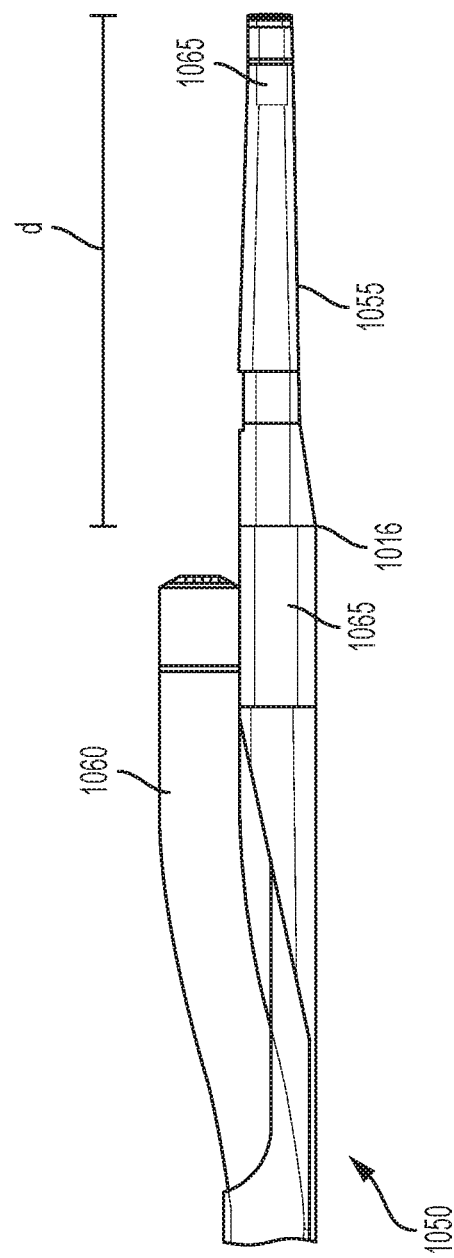
FIG. 3 is a side view of the distal tip portion as shown in FIG. 2B depicting the laser delivery member in an extended position with respect to the prior art elongated housing.
Figure 4:
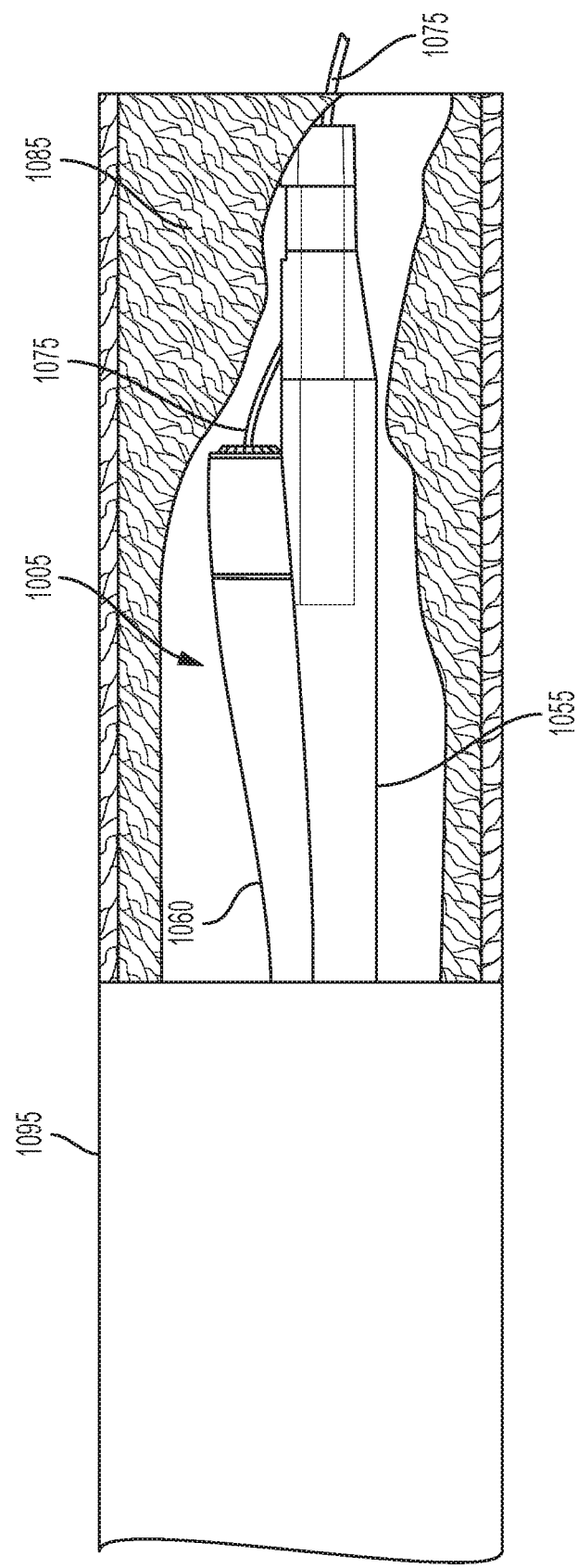
FIG. 4 is a schematic perspective view of a prior art catheter system disposed within the vasculature.

Distal end portion 1050 includes a radial opening, a nosecone 1055 disposed distally of the radial opening, and radiopaque markers 1065 on the proximal and the distal ends of the nosecone 1055, shown in greater detail in FIG. 3 and FIG. 4. FIG. 4 shows catheter system 1000 having a laser delivery mechanism 1005 with a guidewire lumen extending therethrough including the distal end 1060. A guidewire 1075 extends through the guidewire lumen of the laser delivery mechanism 1005 and through a channel and lumen within the nosecone 1055 and out the distal end of the nosecone 1055. A more detailed description of this catheter system 1000 can be seen and is described in U.S. Publication No. 2013/0338500 which is also assigned to the Applicant of this patent application. U.S. Publication No. 2013/0338500 is hereby incorporated by reference for all that it teaches and for all purposes.

Continuing to refer to FIGS. 3 and 4, because the guidewire 1075 travels through both the guidewire lumen of the laser delivery mechanism 1005, wherein the guidewire lumen is disposed within the center of the laser delivery mechanism 1005, and the guidewire 1075 travels through and out the distal end of the nosecone 1055, the length d of the nosecone 1055 is required to be sufficiently long as to accommodate guidewire 1075 traveling through nosecone 1055. The catheter system 1000 shown in FIGS. 1-4, therefore, prevents the distal end of the laser delivery member 1060 from reaching the target matter 1085 in vessel 1095 because the nosecone 1055 is disposed distally of the distal end of the laser delivery member 1060. Accordingly, a long felt need exists to provide a laser delivery member 1060 in a position such that the distal end of the laser delivery member 1060 is adjacent to the nosecone 1055 when the laser delivery mechanism 1005 is parallel with the nosecone 1055.

Referring now to FIGS. 5-10, catheter system 100 is shown having a laser delivery member 90 and an elongated housing 12. The elongated housing 12 includes a central axis between proximal end 14 and distal end 16. Distal end portion 50 of the elongated housing 12 includes a cavity 18 located proximate to the nosecone 16 of elongated housing 12, wherein the nosecone 16 is at the most distal end of the elongated housing 12. Radial opening 18 is referred to as cavity 18 interchangeably herein. The cavity 18 includes a ramp disposed at an angle to the central axis of the elongated housing 12. The angle of the ramp may but need not be the same over the length of the ramp. In an example aspect of the present disclosure, ramp 420 includes a ramp section and apex section, shown in further detail in FIG. 9. Elongated housing 12 includes a nosecone having thickness t, wherein thickness t is minimized, in comparison to the nosecone in FIGS. 1-4, in order that the nosecone extending beyond the cavity 18 is, for example, a rounded tip.

Figure 5:
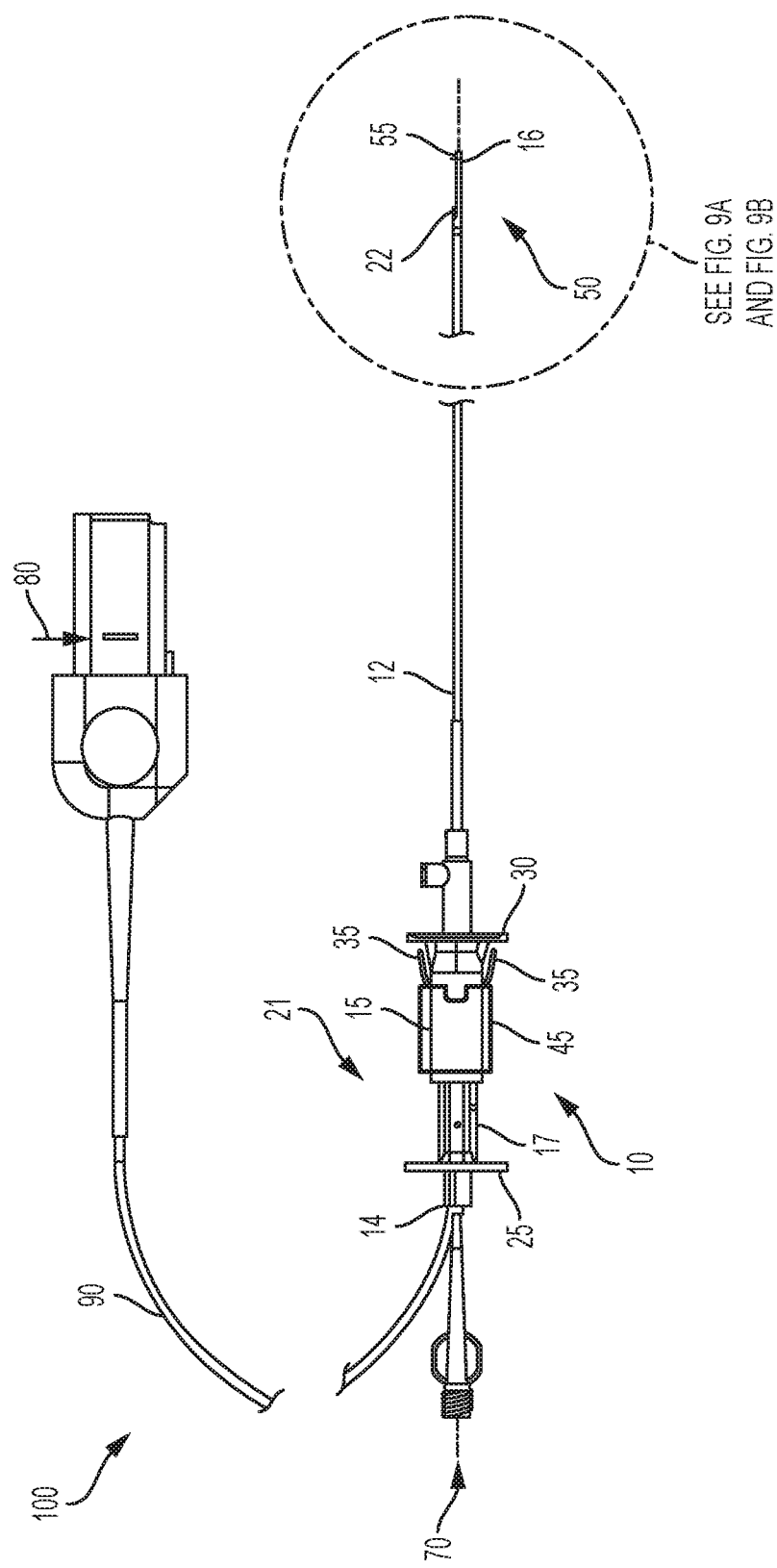
FIG. 5 is a perspective view of a catheter system according to an example aspect of the present disclosure, comprising a laser delivery member and an elongated housing, wherein the elongated housing includes a handle having an actuation mechanism and a lock feature and a distal end having a reduced nosecone configuration.

In an example aspect of the present disclosure, elongated housing 12 may include a guidewire lumen capable of accepting a guidewire. In an example aspect of the present disclosure, the guidewire may be connected to a laser delivery member 90. Referring to FIG. 5, laser delivery member 90 may include optical fibers (not shown), a coupler 80 at its proximal end, laser emitters, such as the exposed ends the optical fibers, at its distal end, and a flexible sheath encapsulating the optical fibers. The optical coupler 80 connects the elongated laser deliver member 90 to a laser generator that provides light energy to the optical fibers. The laser delivery member 90 may also include a bifurcate, which connects a luer adaptor 70 to the flexible sheath. The flexible sheath may include a guidewire lumen (not shown) which is in communication with the opening in the luer adaptor. Accordingly, a guidewire may be inserted into a port in the luer adaptor 70, and the guidewire travels through the guidewire lumen and exit either the laser delivery member 90 or the elongated housing 12.

The bifurcate and/or the laser delivery member 90 is inserted into the handle mechanism 10 of the elongated housing 12. Laser delivery member 90 is movable with respect to the elongated housing 12 in an example aspect of the present disclosure. For example, the distal end 22 of the laser delivery member 90 is advanced to the distal end 16 of the elongated housing 12 in a first position (e.g., advanced position). In a second position, laser deliver member 90 is retracted such that the distal end 22 of the laser delivery member 90 resides in channel 26. The laser delivery member 22 is, therefore, moveable between the first and second positions.

Elongated housing 12 also includes a handle mechanism 10, having proximal disc 25 and distal disc 30. The handle mechanism depicted in FIG. 5 is similar to the handle mechanism discussed hereinabove with respect to FIGS. 1 and 2 except that the handle mechanism in FIG. 5 includes a sleeve 45 to protect the release arms 35 from being inadvertently actuated, and FIG. 1 does not include such sleeve.

In an example aspect of the present disclosure, handle or handle mechanism 10 is associated with proximal end 14 of the elongated housing 12 and includes actuation mechanism 21 coupled to laser delivery member 22. Actuation mechanism 21 comprises body 15 including distal disc 30 and at least one release arm 35, and plunger 17 including proximal disc 25, the plunger disposed at least partially within body 15. In an example aspect of the present disclosure, distally advancing plunger 17 includes depressing proximal disc 25 and distal disc 30 to advance laser delivery member 22. In an example aspect of the present disclosure, actuation mechanism 21 includes moveable lock feature 45, wherein moveable lock feature is operatively connected to body 15.

Figure 9A:
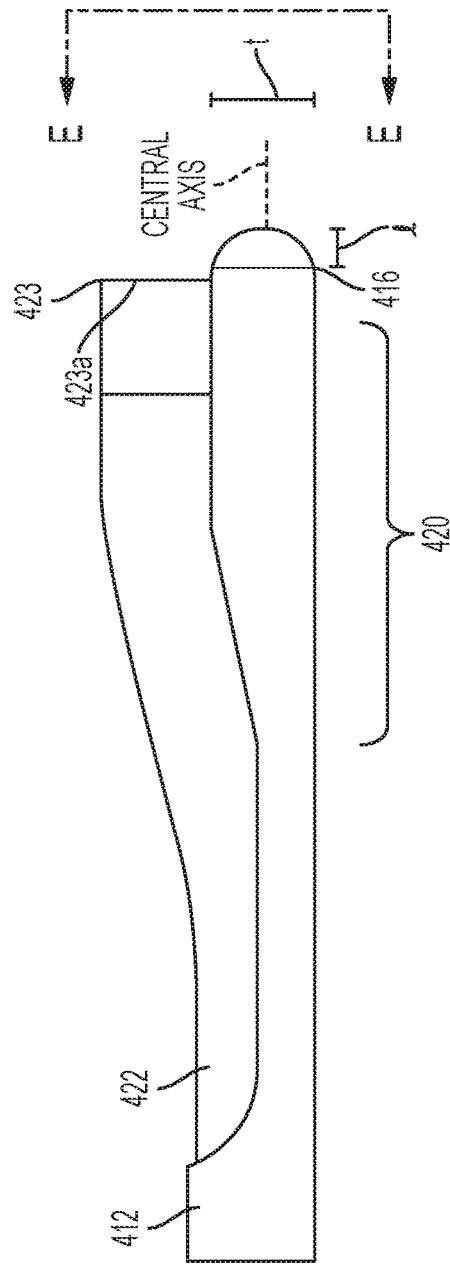
FIG. 9A is a perspective view of a distal end of a laser delivery member in an extended or advanced position with respect to the nose section of the elongated housing according to an example aspect of the present disclosure.
Figure 9B:
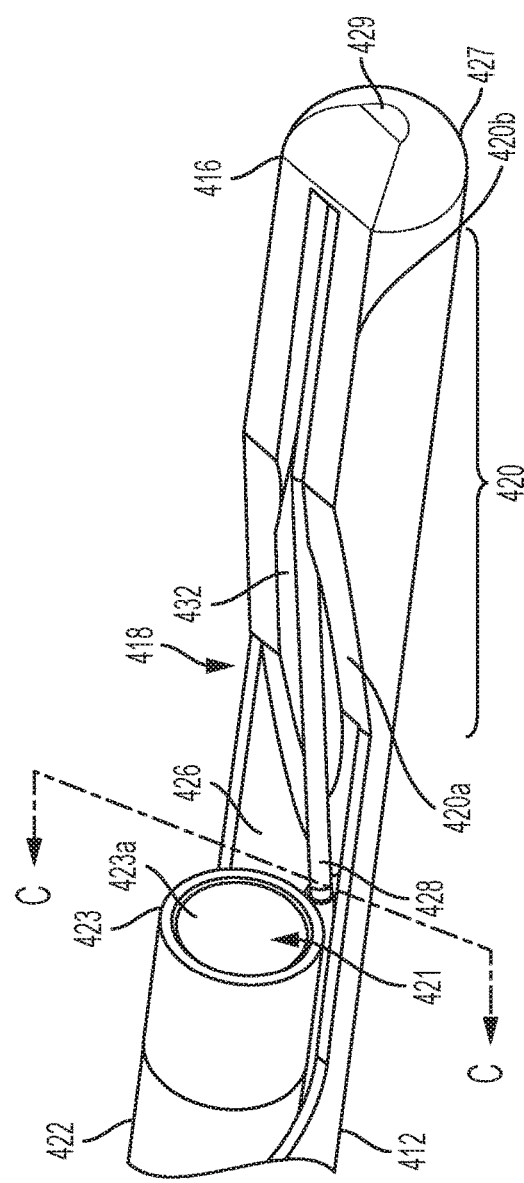
FIG. 9B is a perspective view of a distal end of a laser delivery member in a retracted position with respect to the nose section of the elongated housing according to an example aspect of the present disclosure.

In a first position, moveable lock feature 45 is configured to prevent the at least one release arm 35 from being depressed in order to retain laser delivery member 22 in an advanced position. For example, an advanced position can include laser delivery member 22 being positioned on ramp 420 or at or adjacent the distal end 416 of the nosecone as depicted in FIG. 9A. The ramp 420 may include ramp portion 420a and apex portion 420b. In a second position, moveable lock feature 45 is configured to permit the at least one release arm 35 being depressed to retract laser delivery member 22 (422) to a retracted position as depicted in FIG. 9B. In an example aspect of the present disclosure, laser delivery member 422 is disposed within lumen or channel 426 of the elongated housing 12 (412) proximate the ramp 420. When the handle mechanism 10 is in the position depicted in FIG. 5, wherein the proximal disc 25 and distal disc 30 are not depressed, the handle mechanism 10 is in an unactuated position, and the laser delivery member 22 (422) is in a retracted position within the elongated housing 12 (412), as depicted in FIG. 9B. When the proximal disc 25 and distal disc 30 are depressed, the handle mechanism 10 is in an actuated position, and the laser delivery member 22 (422) is in an actuated position within the elongated housing 12 (412), either approximating the position or at the position depicted in FIG. 9A.

In an example aspect of the present disclosure, laser delivery member 90 is elongated housing 12. The elongated housing 12 and the laser delivery member 90 are introduced coaxially, either sequentially or simultaneously, onto a guidewire and advanced to a target area within a patient's vasculature. The guidewire serves as a tracking guide or 'rail' for the elongated housing 90 and laser delivery member 90 to run over. As will be discussed herein with respect to FIGS. 10 and 11, the guidewire may be inserted through the elongated housing 12 and the laser delivery member 90. For example, if the guidewire is inserted through the laser delivery member 90, then the guidewire may be inserted through the luer fitting 70, which is coupled to the laser delivery member 90. Alternatively, if the guidewire is inserted through the elongated housing 12, then the guidewire may be inserted through the luer fitting 70, if the luer fitting is coupled to the laser delivery member 90, or the guidewire may be inserted through a port in the handle mechanism 10, which is coupled to the elongated housing 12. Guidewires for such uses are known in the art and may comprise those with diameters between about 0.010 and 0.06 inches, with 0.014 and 0.018 inches diameter being typical sizes for artery applications. The guidewires may have bendable tips of coiled wire or plastic and a more rigid shaft of tapered ground stainless steel or other suitable material for push and torque transmission.

Referring to FIGS. 9A-9D, there is depicted an enlarged portion of the distal ends 412, 422 of the elongated housing 12 and the laser delivery member 90, respectfully, of the catheter system depicted in FIG. 5. Continuing to refer to FIGS. 9A-9D, an example aspect of the present disclosure includes a configuration of the elongated housing and the laser delivery member such that the distal end 422 of the of the laser delivery member 90 is either radially aligned with the radial opening 418 in the elongated housing (FIG. 9B) or adjacent the distal end 416 of the elongated housing 412 when the distal end 422 of the laser delivery member 422 is parallel with the distal end 416 of the elongated housing tip 427 (FIG. 9A), thereby facilitating closer proximity and treatment of target matter, for example, in a patient's vasculature.

In an example aspect of the present disclosure, the catheter system illustrated comprises elongated housing 12, 412 having a proximal end (see FIG. 5), a distal end portion, a housing channel 426 disposed between the proximal end and distal end 416, a cavity 418 disposed proximate the distal end of elongated housing 412 and in communication with housing channel 426. In an example aspect of the present disclosure, the distal end has ramp 420 having inclining proximal section 420a and apex section 420b, nose section 427, and a rail wire channel 432 in communication with ramp 420 and housing channel 426. The rail wire channel 432 ends at the nose section 427 and preferably does not pass or go through the nose section 427. The laser delivery member 422, which has a distal end 423, at least one optical fiber 421 therein, is at least partially disposed within housing channel 426 and movable therein. The ramp 420 may be adapted to move the distal end 423 of the laser delivery member 422 laterally (radially) away from the central axis of elongated housing 412 when distal end 423 of laser delivery member 422 moves distally and axially on ramp 420.

In an example aspect of the present disclosure, the catheter system 100 may also comprise a rail wire 428 extending through rail channel 432 and slidably coupled to laser delivery member 422. The rail wire 428 extends through the rail channel 432 in the ramp 420, and the rail wire 428 terminates in the ramp 420 or in the nose section 427. That is, the rail wire 428 does not pass through or extend beyond the nose section 427. In an example aspect of the present disclosure, the nose section 427 is a rounded tip 429 having minimal thickness t and minimal length 1. As shown in FIG. 9B, the laser delivery member 422 may have rail wire lumen disposed on its radial periphery or adjacent its circumference in comparison to having a lumen through the center of the laser delivery member 422 for the rail wire 428 to pass. Alternatively, the rail wire lumen may be disposed eccentrically within the laser delivery member 422, such as between the radial center of the laser delivery member 422 and its circumference. Locating the rail wire lumen either along the circumferential length of the laser delivery member 422 or eccentrically allows the laser delivery member 422 to be disposed closer to the nose section 427.

As discussed above, the catheter system 100, particularly the elongated housing 12 (412) further comprises an actuation mechanism 10 coupled to the proximal end of the elongated housing 12 (412) and the laser delivery member 22 (422). The actuation mechanism 10 has a body 15 and a plunger 17 disposed at least partially within the body 15, whereupon distally advancing or actuating the plunger 17 advances, the laser delivery member 422 travels distally along the rail wire 428, thereby positioning the distal end 423 of the laser delivery mechanism 422 laterally away from the central axis of the elongated housing 412 and generally parallel to the central axis as the second distal end 423 is at, along or beyond the apex section 420b of the ramp 420. FIG. 9C illustrates in cross-section the positioning of rail wire 428 relative to laser delivery member 422 and elongated housing 412 when the laser delivery member is in a retracted position. Similarly, FIG. 9D illustrates the position of rail wire 428 relative to laser delivery member 422 and elongated housing 412 when the laser delivery member is in a retracted position, wherein the rail wire 428 extends to distal end of the ramp 420.

Figure 11:
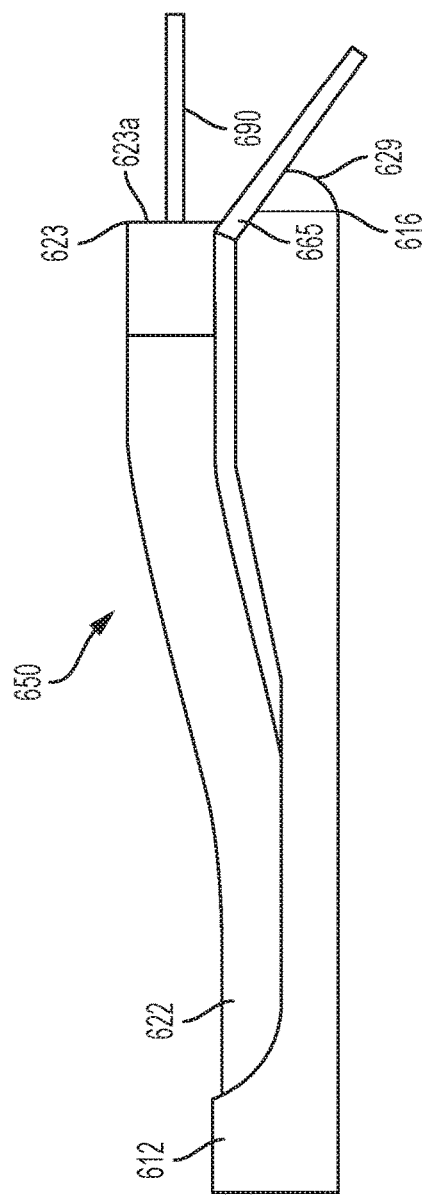
FIG. 11 is a side view of a distal end of a laser delivery member in an advancing position with respect to the nose section of the elongated housing according to an example aspect of the present disclosure, wherein the laser delivery member includes a rail wire lumen (not shown) and the elongated housing includes a guidewire lumen and an side channel for optionally including a guidewire exiting therefrom (not shown), wherein the laser delivery member is advanced onto the ramp and includes a guidewire exiting therefrom.
Figure 12:
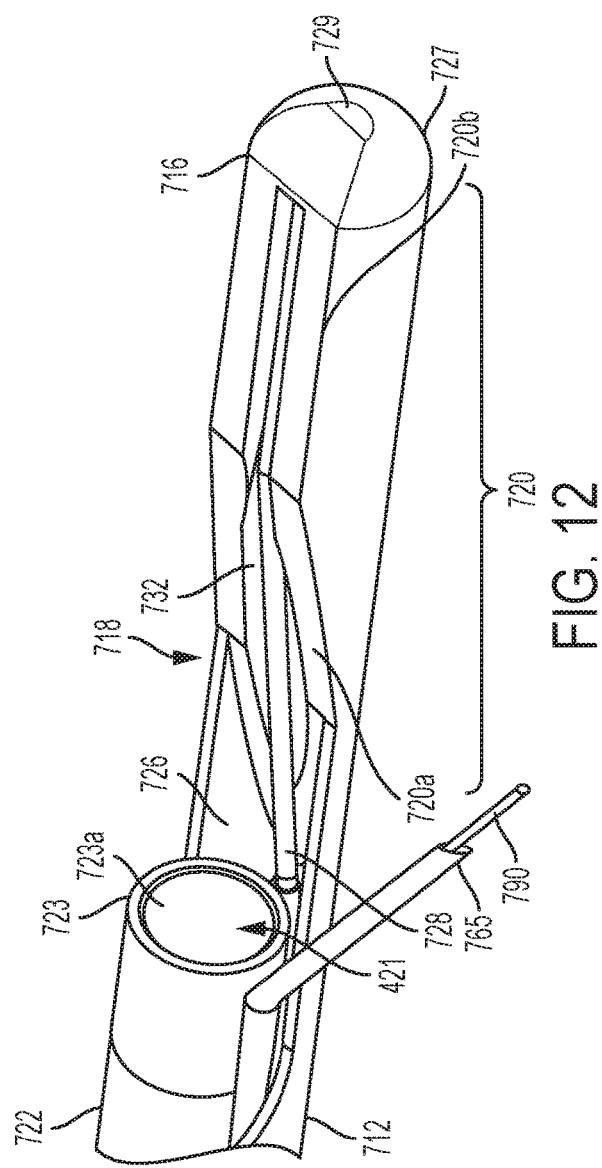
FIG. 12 is a perspective view of a distal tip of a laser delivery member in an advancing position with respect to the nose section of the elongated housing according to an example aspect of the present disclosure, wherein the elongated housing includes a side channel having a lumen though which both the rail wire, which is coupled to the elongated housing, and the guidewire pass therethrough, wherein the laser delivery member is advancing to the ramp section.

In another example aspect of the present disclosure, elongated housing 412 may further comprise a guidewire channel (shown as 544 in FIG. 10A) exiting through the laser delivery member. Alternatively, the guidewire channel includes a side port (as shown in FIGS. 11 and 12). Optionally the guidewire channel may be in communication with the ramp. In yet another example aspect of the present disclosure, elongated housing further comprises a sheath, wherein the guidewire channel is disposed within the sheath. Advantageously, the guidewire channel does not pass through the nosecone.

Continuing to refer to FIGS. 9A and 9B, in an example aspect of the present disclosure, assuming that the elongated housing 412 includes a guidewire lumen, the elongated housing 412 is introduced onto and over the guidewire and advanced to or near the treatment site within the patient's vasculature. The laser delivery member 422 may already be coupled to the elongated housing 412 upon the elongated housing's introduction and advancement to the treatment site via the rail wire 428. If the laser delivery member 422 is not already coupled to the elongated housing 412, then the laser delivery member 422 is introduced onto the rail wire 428 so as to be disposed within channel 426 extending through the elongated housing 412. The laser delivery member 22 is then advanced along the rail wire 428 such that the distal end 423 of the laser delivery member 422 becomes supported by the ramp 420 at any angle between 1 degree and 90 degrees in relation to the central axis of the elongated housing 412. In an example aspect of the disclosure, by employing ramp 420 having different exit angles from the associated channel 426, different angles and/or offsets may be selected for treating a target area after the catheter 100 has been located within a vessel of a patient. In some embodiments, without limitation, the ramp 420 may be adjustable, as one example only, the ramp 420 may be slidable to allow varying degrees of offset. The ramp 420 may be formed or fused to the internal wall of the housing 412 and made from metal, plastic, rubber, and the like.

Laser energy is then applied to the treatment site through the at least one optical fiber 421 according to methods and protocols known to those of ordinary skill in the art. In an example aspect of the present disclosure, without limiting the scope of the disclosure, in conjunction with the application of laser energy, the position of the laser delivery member 422 is optionally varied by the user (i) translating the laser delivery member 422 proximally or distally in order to adjust the angle and location of disposition of its distal end 423 with respect to the targeted ablation area. Optionally, the offset of the central axis of the tip of the laser delivery member 422 from the central axis of elongated housing 412 may be varied by adjusting the distance that the laser delivery member 422 travels on ramp 420 while keeping the central axis of the tip substantially parallel to the central axis of the elongated housing 412. In an example aspect of the present disclosure, catheter system 100 containing laser delivery member 422 is optionally rotated along its central axis during the laser treatment, thereby applying laser energy to areas of the treatment site within the arc of the rotation.

The elongated housing 412 is an elongated structure having a lumen or channel 426 large enough to accommodate the laser delivery member 422 and rail wire 428 for tracking the laser delivery member 22 and optionally a guidewire. Channel 426 extends the entire length of the elongated housing 12 (412) from the proximal end 14 to the distal end 16. Various control mechanisms including electrical, optical, and mechanical control mechanisms may be employed with the elongated housing 412 permitting the catheter system 100 to be specifically directed to a target area (see FIG. 4) within the vasculature. In an example aspect of the present disclosure, the housing is made from any rigid, semi-flexible, or flexible material including a combination thereof made from a material including metal, plastic, rubber, and the like. Round or flat metal ribbon wire may be embedded within the material, inserted through the cavity 418, or disposed at the distal end 16 to add stability to the elongated housing 12 at the distal end 16. The first distal end 416 of the housing 412 may be formed from plastic, metal, or any combination thereof. When metal is used, materials must be selected to provide appropriate flexibility without producing failure since the cavity 418 tends to reduce the structural integrity of some portions of the housing 412. Thus, in some embodiments, the first distal end 416 comprises a shape memory alloy, as one example only, nickel-titanium alloy. In other embodiments, without limitation, the first distal end 416 may comprise a stent-like structure proximal, distal, within, or a combination of such proximate the cavity 418. The stent-like structure may be made from at least one of stainless steel, cobalt-chromium, nickel titanium, and the like.

The length of the elongated housing 12 may be varied as desired. The elongated housing 12 may be one piece or have a plurality of sections including a support structure section at the distal end 16 as discussed further below. The distal end 16 of the elongated housing 12 may include a non-traumatic polymer tip separate or integrated into the housing 12. This allows the forces seen in bending to be dissipated throughout the structure, reducing stress risers that could cause failure. The housing 12 may also include at least one wire disposed within the channel 26 to add robustness to the housing 12. The channel 426 is in communication with cavity 418 and rail wire channel 432. The channel 426 is open to the exterior of the housing 412 through the cavity 418.

Referring again to FIG. 5, in an example aspect of the present disclosure, actuation mechanism 21 further comprises a spring (not shown) disposed within body 15. The actuation mechanism 21 may further comprise at least one detent 40 per release arm 35. In an example aspect of the present disclosure in the first position, the at least one detent is engageable with an internal body feature having grooves and/or ridges. In an example aspect of the present disclosure, a lock feature 45 is configured to slide, rotate, or both to move from the first position to the second position. In an example aspect of the present disclosure, lock feature 45 is a sleeve disposed circumferentially over body 45. In an example aspect of the present disclosure, the sleeve restricts movement of the release arm or the detent in the first position. Lock feature 45 may take the form of various embodiments or aspects. Without being limiting, in an example aspect of the present disclosure, the sleeve is a rotatable cylindrical sleeve configured to cover but not contact the at least one release arm in the first rotatable position. Example aspects of the present disclosure include lock features as shown in FIGS. 6-8.

Figures 6C, 6D, 6E:
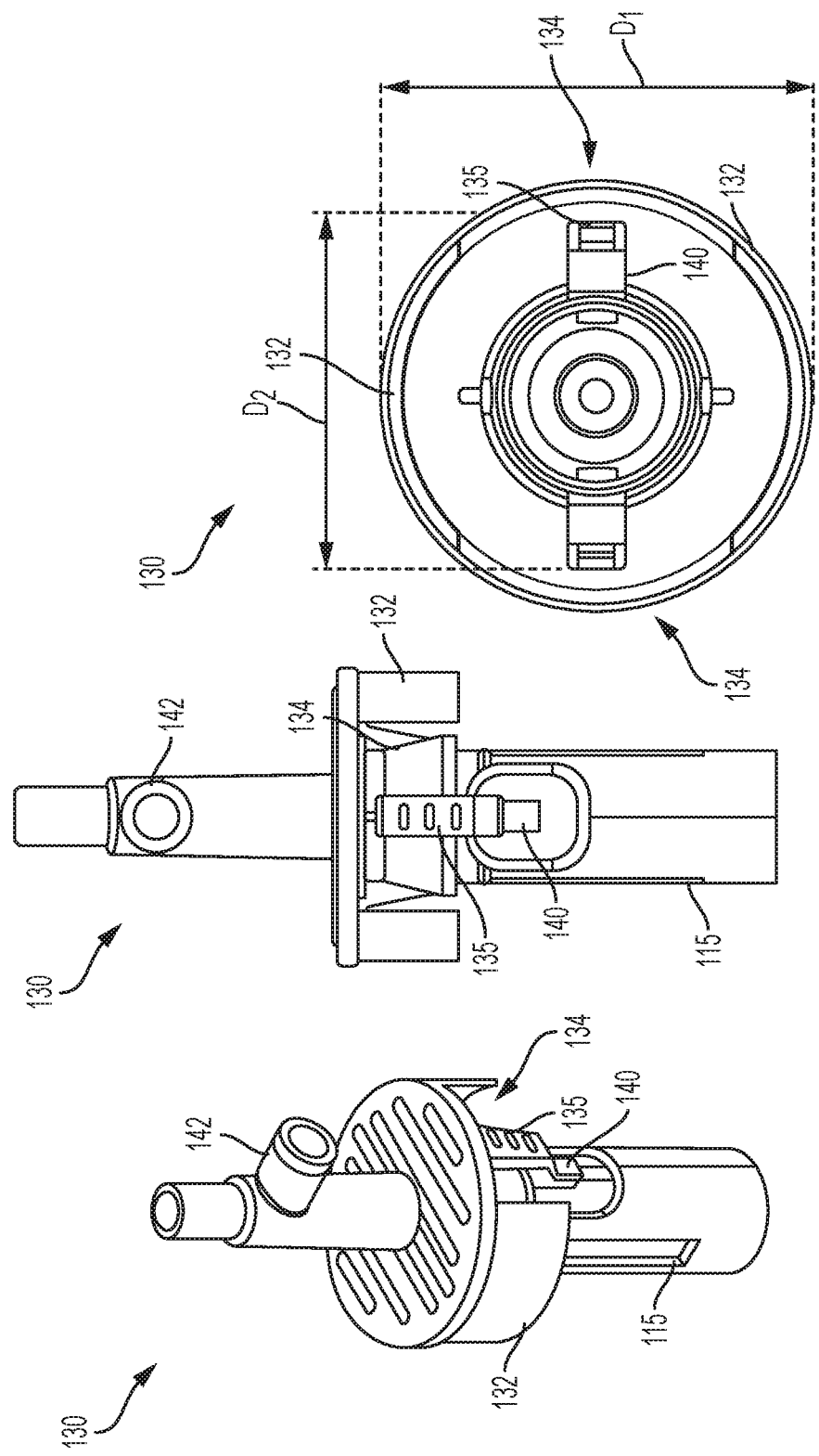
FIG. 6C is another perspective view of the actuation mechanism body and rotatable sleeve disc depicted in FIG. 6B.
FIG. 6D is a side view of the actuation mechanism body and rotatable sleeve disc depicted in FIG. 6B.
FIG. 6E is a bottom view of the actuation mechanism body and rotatable sleeve disc depicted in FIG. 6B.
Figure 6F:
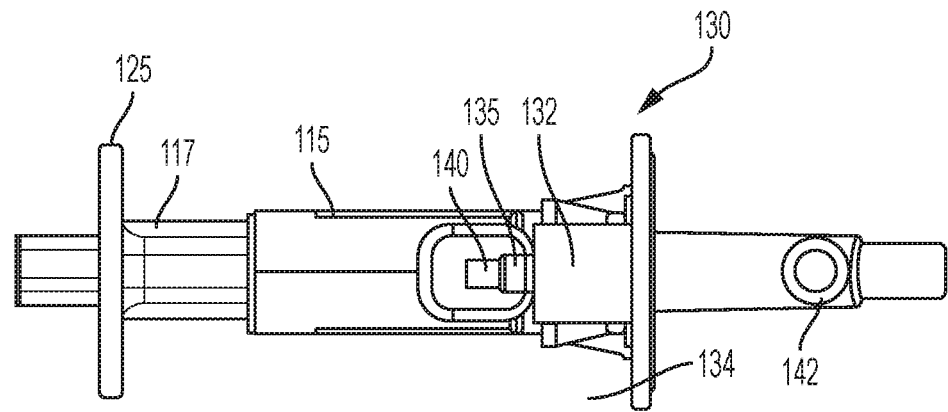
FIG. 6F is a side view of an actuation mechanism having the sleeve depicted in FIG. 6A, wherein the sleeve is aligned relative to the release arms to prevent the release arms from being depressed.
Figure 6G:
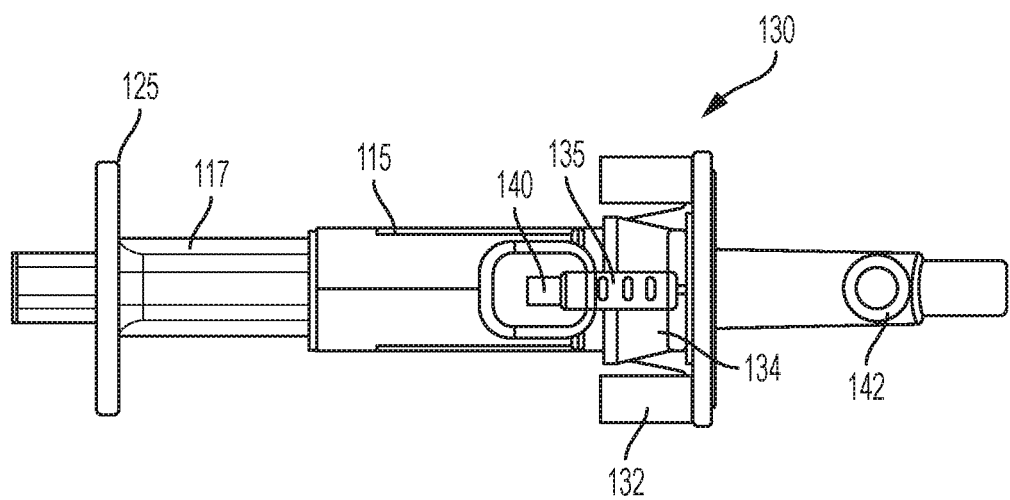
FIG. 6G is a side view of the actuation mechanism and sleeve depicted in FIG. 6F, wherein the sleeve is offset relative to the release arms to allow the release arms being depressed. The sleeve of FIG. 6G is offset or rotated 90° relative to the sleeve of FIG. 6F.

FIG. 6A is a perspective view of distal disc 130 having a rotatable sleeve according to an example aspect of the present disclosure. As illustrated, rotatable sleeve 130 is integrally formed with distal disc 130. Alternatively, the rotatable sleeve can be formed as a separate piece or part. A catheter such as shown in FIG. 5 comprising an elongated housing having a first proximal end and a first distal end, the elongated housing having a lumen disposed between the first proximal end and the first distal end, the lumen having an opening at the first distal end; a laser delivery member having a second proximal end and a second distal end, the laser delivery member being at least partially disposed within the lumen and movable therein; and a handle associated with the first proximal end and having an actuation mechanism coupled to the laser delivery member is suitable for use with the distal disc of FIG. 6A. FIG. 6B is a perspective view of an actuation mechanism body including a distal disc as shown in FIG. 6A having a rotatable sleeve according to an example aspect of the present disclosure. FIG. 6B illustrates an actuation mechanism comprising body 115 including distal disc 130 and at least one release arm 135, distal disc 130 including a rotatable cylindrical sleeve 132 extending proximally therefrom and having at least one window 134. FIGS. 6C-6E show alternate views of body 115 including distal disc 130 having a rotatable sleeve according to an example aspect of the present disclosure. FIG. 6C illustrates distal disc 130 on body 115 as a top view, FIG. 6D as a side view, and FIG. 6E as a bottom view of an actuation mechanism body including distal disc 130. Cylindrical sleeve 132 has a diameter $D_1$ greater than the distance $D_2$ between the outermost portions of release arms 135. Release arms 135 are configured as cantilevers, and release arms are interchangeably referred to as cantilevers herein. When proximal disc 125 (not shown) and distal discs 130 are depressed, the spring contracts and detents extending from the release arms engage with an internal body feature having grooves and/or ridges to hold the spring tight. When the cantilevers or release arms are depressed, the detents disengage from the internal body feature and a plunger is retracted as is the laser deliver member, thus releasing the spring. Therefore, sleeve 132 protects release arms 135 or cantilevers from being inadvertently or accidentally depressed during use when sleeve 132 is aligned with release arms 135 in a first position. FIG. 6E shows a second position, wherein the sleeve is rotated so that windows 134 are aligned with release arms 135 therefore allowing access to depress release arms as desired. In an example aspect of the present disclosure, a plunger including a proximal disc is also included (not shown). The plunger, disposed at least partially within body 115, is coupled with body 115. In an example aspect of the present disclosure, distally advancing the plunger includes depressing the proximal disc and the distal disc to advance the laser delivery member. In an example aspect of the present disclosure, in a first rotatable position, the at least one window is offset relative to the at least one release arm; the release arm configured to being protected to prevent being depressed. In an example aspect of the present disclosure, rotatable cylindrical sleeve 132 is configured to cover but not engage, activate or contact the at least one release arm in the first rotatable position. In an example aspect of the present disclosure, in a second rotatable position, the at least one window is aligned relative to the at least one release arm, the release arm configured to being depressed to retract the laser delivery member (see FIG. 6E). In an example aspect of the present disclosure, the actuation mechanism further comprises a spring disposed within the body. In an example aspect of the present disclosure, the at least one release arm 135 further includes at least one detent 140 wherein the at least one detent is engageable with the spring in the first rotatable position. Body 115 also includes flush port 142. FIG. 6F is a side view of an actuation mechanism having the sleeve depicted in FIG. 6A, wherein the sleeve is aligned relative to the release arms to prevent the release arms from being depressed. FIG. 6G is a side view of the actuation mechanism and sleeve depicted in FIG. 6F, wherein the sleeve is offset relative to the release arms to allow the release arms being depressed. The sleeve of FIG. 6G is offset or rotated 90° relative to the sleeve of FIG. 6F.

Figure 7D:
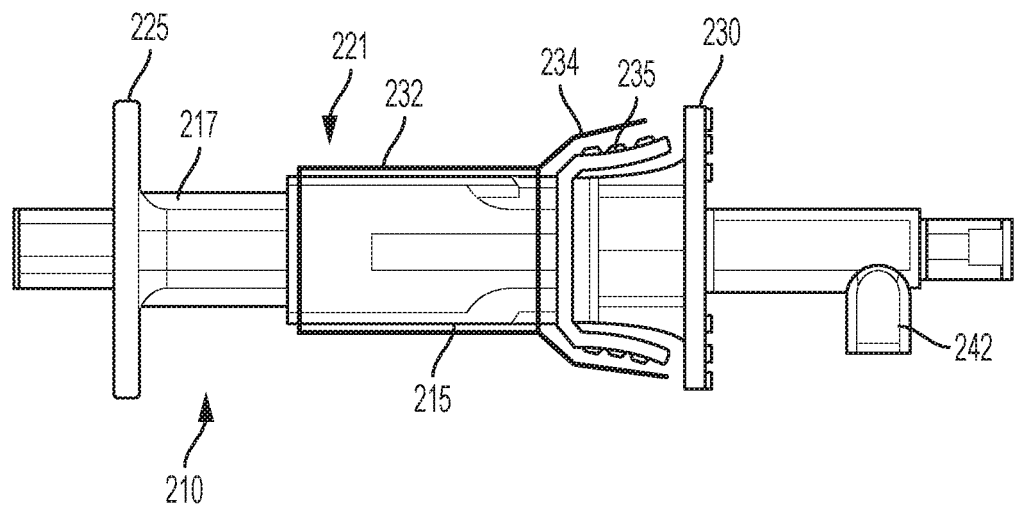
FIG. 7D is a side view of the actuation mechanism and sleeve depicted in FIG. 7A, wherein the protector arms are aligned relative to the release arms to prevent the release arms from being depressed.
Figure 7E:
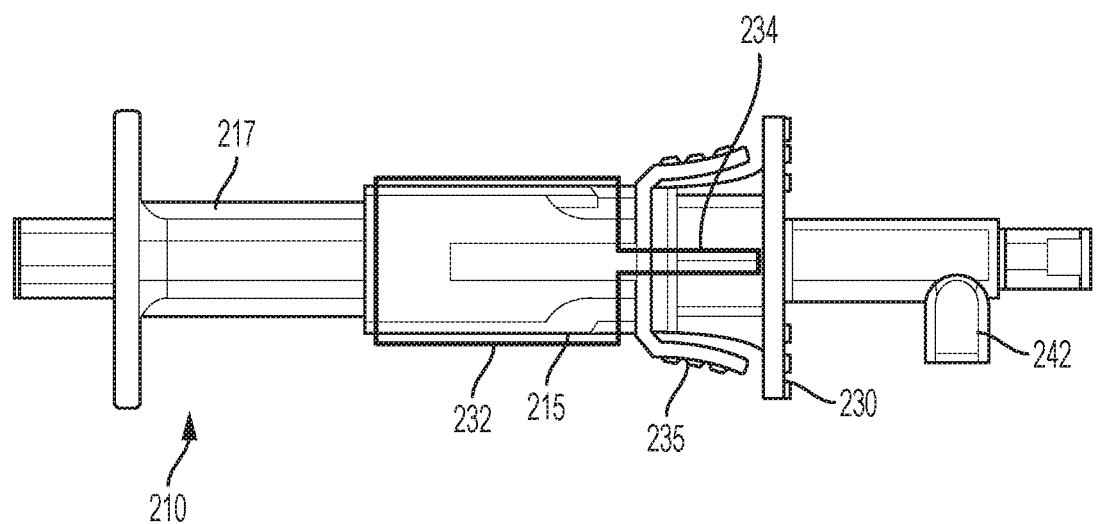
FIG. 7E is a side view of the actuation mechanism and sleeve depicted in FIG. 7A, wherein the protector arms are offset relative to the release arms to allow the release arms being depressed. The sleeve of FIG. 7E is offset or rotated 90° relative to the sleeve of FIG. 7D.

In another example aspect of the present disclosure, FIG. 7A is a perspective view of sleeve 232 having protector arms 234 for an actuation mechanism lock feature. FIG. 7B shows a side view and FIG. 7C shows a bottom view of sleeve 232 as shown in FIG. 7A. As illustrated, for example, sleeve 232 is a piece formed separately from the handle and fits over or circumferentially around a body 215 (see FIGS. 7D and 7E) and includes protector arms 234. As one of skill in the art appreciates, protector arms 234 are integrally formed with sleeve 232 or alternatively formed separately and then fixed to sleeve 232. In an example aspect of the present disclosure, the sleeve of FIG. 7E is offset or rotated 90° relative to the sleeve of FIG. 7D. Alternatively, sleeve 232 may be slid to move protector arms in place over the release arms and then retracted proximally to allow access to depress and release the release arms, as one skilled in the art would appreciate.

Referring to FIGS. 7A-7E, in an example aspect of the present disclosure, a catheter comprises an elongated housing having a first proximal end and a first distal end, the elongated housing having a lumen disposed between the first proximal end and the first distal end, the lumen having an opening at the first distal end. In an example aspect of the present disclosure, the laser delivery member has a second proximal end and a second distal end, the laser delivery member being at least partially disposed within the lumen and movable therein. In an example aspect of the present disclosure, handle 210 is associated with the first proximal end and includes actuation mechanism 221 coupled to the laser delivery member. The actuation mechanism comprises body 215 including distal disc 230 and at least one release arm 235; and plunger 217 including proximal disc 225, the plunger 217 disposed at least partially within body 215; where distally advancing plunger 217 includes depressing the proximal disc 225 and the distal disc 230 to advance the laser delivery member. In an example aspect of the present disclosure, actuation mechanism 221 further includes moveable sleeve 232 disposed about body 215 and including at least one protector arm 234 protruding distally therefrom. In an example aspect of the present disclosure in a first position, the at least one protector arm 234 is aligned relative to the at least one release arm 235; the release arm configured to being protected to prevent being depressed. In an example aspect of the present disclosure, the at least one protector arm 234 is configured to cover but not contact the at least one release arm 235 in the first position. In an example aspect of the present disclosure in a second position, the at least one protector arm 234 is offset relative to the at least one release arm 235, the release arm configured to being depressed to retract the laser delivery member as desired by user. In an example aspect of the present disclosure, moveable sleeve 232 is rotatable, slidable, or both. In an example aspect of the present disclosure, actuation mechanism 221 further comprises a spring disposed within body 215 (not shown). In an example aspect of the present disclosure, the at least one release arm 235 further includes at least one detent 240 wherein the at least one detent is engageable with the spring in the first position.

Figure 8D:
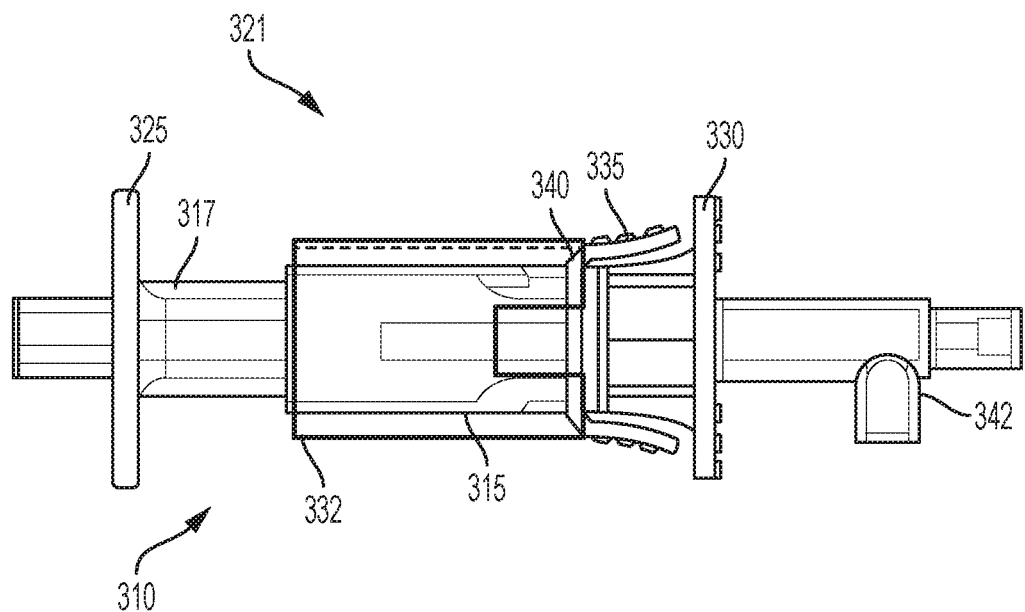
FIG. 8D is a side view of an actuation mechanism including the sleeve depicted in FIG. 8A, wherein the groove is in contact with the detent to prevent one or more release arms from being depressed according to an example aspect of the present disclosure.
Figure 8E:
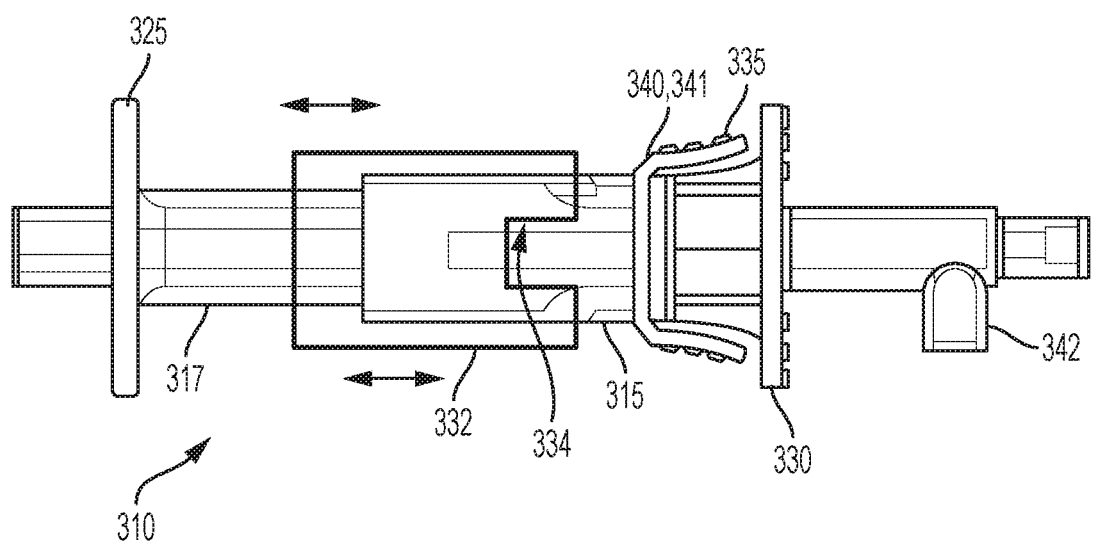
FIG. 8E is a side view of an actuation mechanism including the sleeve depicted in FIG. 8A, wherein the groove is in offset and not in contact with the detent to allow the release arm being depressed according to an example aspect of the present disclosure. The sleeve of FIG. 8E is offset or moved distally relative to the sleeve of FIG. 8D.

FIG. 8A is a perspective view of a sleeve including an internal groove for impinging a detent of a release arm for an actuation mechanism according to an example aspect of the present disclosure. FIG. 8B shows a side view and FIG. 8C a top view of sleeve 332 of FIG. 8A. In an example aspect of the present disclosure, the groove 334 is circumferential, and may be continuous or discontinuous. Groove 334 is positioned proximally from distal portion 336 of sleeve 332. In an example aspect of the present disclosure, a catheter comprises an elongated housing having a first proximal end and a first distal end, the elongated housing having a lumen disposed between the first proximal end and the first distal end, the lumen having an opening at the first distal end; a laser delivery member having a second proximal end and a second distal end, the laser delivery member being at least partially disposed within the lumen and movable therein; and handle 310 associated with the first proximal end and having an actuation mechanism coupled to the laser delivery member. The sleeve of FIG. 8E is offset or moved distally relative to the sleeve of FIG. 8D. Referring to FIGS. 8A-8E, actuation mechanism 321 comprises body 315 including distal disc 330 and at least one release arm 335 having at least one detent 340 and plunger 317 including proximal disc 325, the plunger disposed at least partially within body 315; where distally advancing the plunger includes depressing the proximal disc and the distal disc to advance the laser delivery member. In an example aspect of the present disclosure, slidable sleeve 332 is disposed about body 315 and includes at least one internal circumferential groove 334. In an example aspect of the present disclosure in a first slidable position, external surface 341 of the at least one detent 340 is in contact with the at least one internal circumferential groove 334. The at least one internal circumferential groove 334 is configured to restrict movement and to prevent the at least one release arm 335 being depressed. In an example aspect of the present disclosure in a second slidable position, external surface 341 of the at least one detent 340 is not in contact with the slidable sleeve 332. Therefore, the release arm 335 is configured to being depressed to retract the laser delivery member as desired by the user. In an example aspect of the present disclosure, actuation mechanism 321 further comprises a spring (not shown) disposed within body 315. In an example aspect of the present disclosure, the at least one detent is engageable with the spring in the first rotatable position. In an example aspect of the present disclosure, slidable sleeve 332 further comprises windows 338. Windows 338 allow for rotation of the sleeve, in addition to or instead of sliding of the sleeve, to move from a first position to a second position.

In any of the aspects above related to the catheter proximal end in the area of the handle, a first position of the actuation mechanism correlates to the laser delivery member being advanced to close proximity with a target matter, for example, in a patient's vessel. In an example aspect of the present disclosure, an occlusion in the vessel is ablated. In any of the aspects above, the second position of the actuation mechanism for the handle correlates to the laser delivery member being retracted. In the retracted position, the catheter is readily repositioned or removed. In any of the aspects above, the laser delivery member may be advanced and/or retracted reversibly and repeatedly giving the user more control. The lock feature, as in any of the aspects above, prevents inadvertent actuation of the release arms, which would trigger retraction of the laser delivery member prematurely during use.

Referring again to FIG. 9A-D, in an example aspect of the present disclosure, a catheter system 100 features facilitating closer proximity and treatment of target matter, for example, in a patient's vasculature. In an example aspect of the present disclosure, a catheter comprises elongated housing 412 having a proximal end (see FIG. 5, proximal end 14), distal end 416, a central axis, and housing channel 426 disposed between the proximal end and distal end 416, cavity 418 disposed proximate distal end 416 of elongated housing 412 and in communication with housing channel 426. In an example aspect of the present disclosure, the distal end or end portion of the elongated housing 412 has ramp 420 having inclining proximal section 420a and apex section 420b, nose section 427, and a rail wire channel 432 in communication with ramp 420. In an example aspect of the present disclosure, the catheter system 100 further comprises laser delivery member 422 having a proximal end (not shown), a distal end 423, at least one optical fiber 421 therein, wherein the laser delivery member 422 is at least partially disposed within housing channel 426 and movable therein. In an example aspect of the present disclosure, ramp 420 is adapted to move the distal end 423 of laser delivery member 422 laterally away from the central axis of elongated housing 412 when distal end 423 of laser delivery member 422 is on ramp 420. In an example aspect of the present disclosure, the catheter system further comprises an actuation mechanism that couples the elongated housing 12, 412 to the laser delivery member 22, 422. In an example aspect of the present disclosure, the actuation mechanism 21 is coupled to or incorporated into a handle 10 of the elongated housing 12. The actuation mechanism 21 has a body 15 and a plunger 17 disposed at least partially within the body 15, whereupon distally advancing the plunger 17 advances the laser delivery member 422 along the rail wire 428. Fixing the end of the rail wire 428 to the distal end of the ramp 420 or the nose section 427 assists in positioning the distal end 423 of the laser delivery member 422 laterally away from and generally parallel to the central axis at or beyond the apex section 420b of the ramp.

Figure 10A:
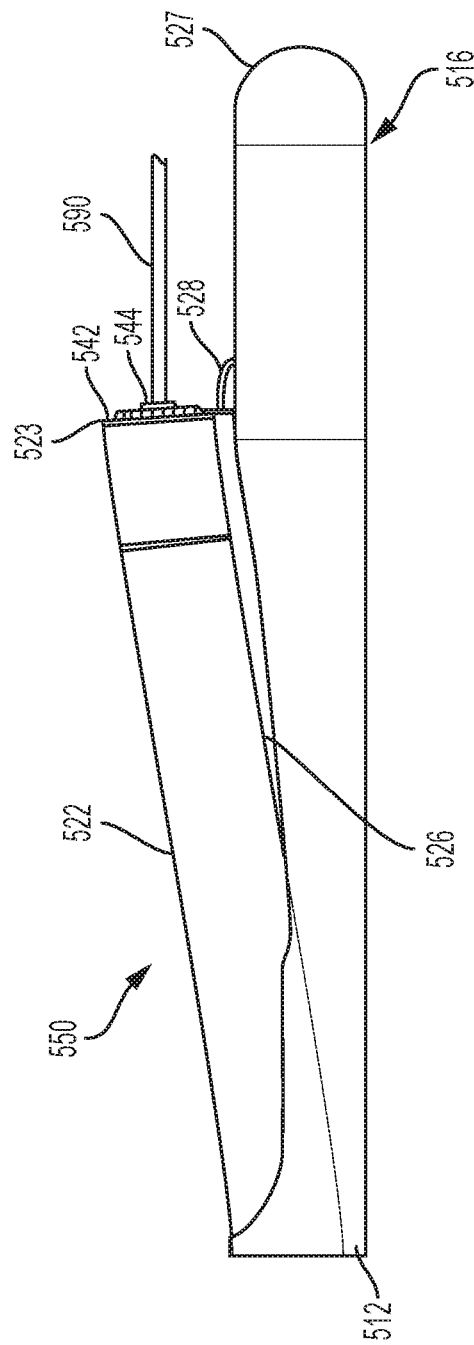
FIG. 10A is a side view of a distal end of a laser delivery member in an advancing position with respect to the nose section of the elongated housing according to an example aspect of the present disclosure, wherein the elongated housing includes a guidewire lumen and a guidewire exiting therefrom.
Figure 10B:
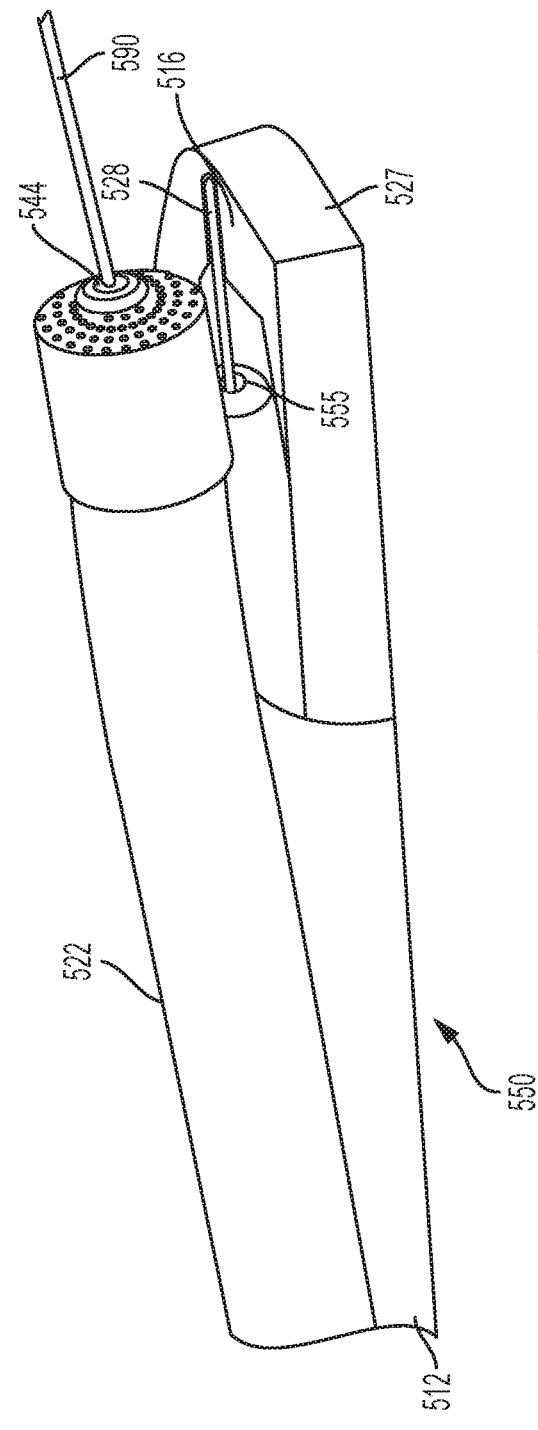
FIG. 10B is a perspective view of a distal tip of a laser delivery member in an advancing position with respect to the nose section of the elongated housing according to an example aspect of the present disclosure, wherein the elongated housing includes a rail wire coupled to the laser delivery member and the elongated housing includes a guidewire lumen and a guidewire exiting therefrom, wherein the laser delivery member is advanced to the nose section.

Referring to FIG. 10A-B, in another example aspect of the present disclosure, a distal tip 550 of catheter system 100 may comprise an elongated housing 512 having a proximal end (see FIG. 5, proximal end 14), a distal end 516, a central axis, and housing channel 526 disposed between the proximal end and distal end 516, cavity 518 disposed proximate first distal end 516 of elongated housing 512 and in communication with the housing channel 526. Optionally, laser delivery member 522 includes a guidewire channel or lumen 565 through and from which guidewire 590 extends. The distal end 516 may have a ramp 520 that includes inclining proximal section 520a and apex section 520b, nose section 527, and a rail wire channel 526 in communication with ramp 520. The rail wire 528 is attached to the distal end 516 or nose section 527. The catheter system 100 may further comprise laser delivery member 522 having a proximal end (not shown), a distal end 523, at least one optical fiber 521 (and preferably a plurality of optical fibers) therein, a lumen 544 extending therethrough, and a rail channel or lumen 555 through and from which rail wire 528 extends. The rail channel 555 depicted in FIGS. 10A and 10B is disposed along the periphery of the laser delivery member 522 such that the rail channel 555 is radially offset from the lumen 544.

Referring to FIG. 11, the catheter system 100 in this figure is different in comparison to the catheter system 100 in FIGS. 10A and 10B in that the guidewire 628 in FIG. 11 extends through and from lumen 644 in the laser delivery device 622, wherein the lumen 644 is disposed in the radial center of the laser delivery device and also includes a side port or exchange port 665 through which the guidewire 690 may alternatively extend. Similar to FIGS. 10A and 10B, the rail wire (as seen as 728 in FIG. 12) is attached to the distal end 616 or nose section 627. Referring to FIG. 11, the elongated housing 612 includes a side port or exchange port 665 having a lumen through and from which guidewire 690 extends.

Referring to FIG. 12, the catheter system 100 in this figure is different in comparison to the catheter system 100 in FIGS. 10A, 10B and 11. The catheter system 100 in FIG. 12 includes an elongated housing 712 having a guidewire lumen as a side port 765. The elongated housing includes a rail wire 728, which is attached to the distal end 716 or nose section 727. The guidewire 790 in FIG. 12 does not pass through the distal end 716 of the elongated housing 712, using side port 765 to extent through instead. While not shown, an example aspect of the present disclosure may include a single wire that acts as both a rail wire and guidewire, wherein the single wire passes through both the lumen 744 of the laser delivery device 722 and the distal end 716 of the elongated housing 712.

Figure 13:
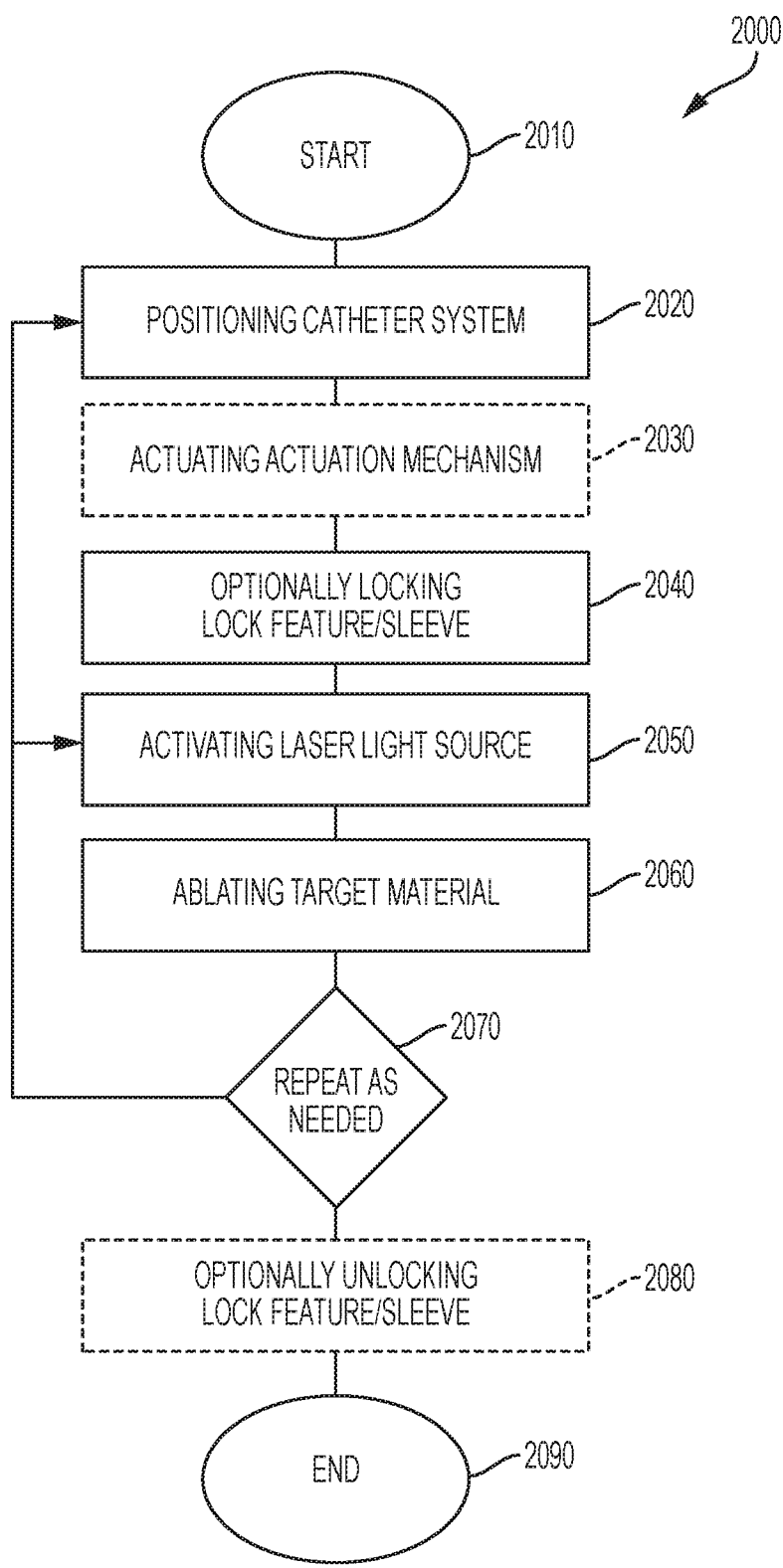
FIG. 13 is a flow chart of performing an ablation procedure using a catheter system of the present disclosure.

In an example aspect of the present disclosure, a method is described in accordance with FIG. 13. The method 2000 comprises positioning a catheter system 2020 within a vessel, wherein the catheter system includes: an elongated housing having a first proximal end, a first distal end, a central axis, and a housing channel disposed between the first proximal end and the first distal end, a cavity disposed proximate the first distal end of the elongated housing and in communication with the housing channel. The catheter further includes the first distal end having: a ramp having an inclining proximal section and an apex section; a nose section disposed distally of the ramp; and a rail wire fixedly attached to and terminating at the ramp or nose section. The catheter further includes a laser delivery member having a second proximal end, a second distal end, at least one optical fiber, the laser delivery member being at least partially disposed within the housing channel and movable therein, the ramp adapted to move the second distal end of the laser delivery member laterally away from the central axis of the elongated housing when the distal end of the laser delivery member is on the ramp; and the rail wire extending through a rail wire channel and slidably connected to the laser delivery member. The method further comprises actuating the actuation mechanism 2030, the actuation mechanism coupled to the elongated housing and the laser delivery member and including a body and a plunger disposed at least partially within the body, whereupon distally advancing the plunger advances the laser delivery member along the rail wire, the rail wire being adapted to position the second distal end laterally away from and generally parallel to the central axis as the second distal end is at or beyond the apex section of the ramp; and activating a laser light source 2050 to generate light energy to ablate target material within the vessel. In an example aspect of the present disclosure, the first distal end has a first distal edge, the first distal edge defining a line extending therefrom and generally perpendicular to the central axis, and the second distal end has a second distal edge, wherein distally advancing the plunger advances the second distal edge to the line. In an example aspect of the present disclosure of the method, the rail wire extends through the ramp but not the nose section. In an example aspect of the present disclosure of the method, the nose section is a rounded tip having minimal thickness. In an example aspect of the present disclosure of the method, positioning the catheter includes the laser delivery member being proximate to the target material, separated only by the minimal thickness of the rounded tip of the nose section. The steps are repeated as needed 2070 to affect or remove the target material as desired. As shown in FIG. 13, the method optionally includes locking a lock feature or sleeve 2040 in a manner as described above to prevent release arms being depressed inadvertently and/or unlocking a lock feature or sleeve 2080 to allow release arms being depressed as desired to retract the laser delivery member.

From the above description, one skilled in the art can easily ascertain the essential characteristics of the present disclosure, and without departing from the spirit and scope thereof, can make various changes and modifications of the disclosure to adapt it to various usages and conditions. Thus, other aspect or embodiments are also considered to be within the scope of the present claims. For example, the laser delivery member of the present disclosure could be replaced with a liquid light guide catheter, or a different type of ablation device or catheter, such as a radiofrequency ablation catheter, microwave ablation catheters, and cryoablation catheters.

What is claimed is:

1. A catheter system comprising:
    an elongated housing having:
        a first proximal end, a first distal end, a central axis, and a housing channel disposed between the first proximal end and the first distal end, a cavity disposed proximate the first distal end of the elongated housing and in communication with the housing channel;
        the first distal end having:
            a ramp having an inclining proximal section and an apex section;
            a nose section; and
            a rail wire channel in communication with the ramp but not the nose section;
    a laser delivery member having:
        a second proximal end, a second distal end, at least one optical fiber, the laser delivery member being at least partially disposed within the housing channel and movable therein, the ramp adapted to move the second distal end of the laser delivery member laterally away from the central axis of the elongated housing when the distal end of the laser delivery member is on the ramp;
    a rail wire fixedly attached to and terminating at the first distal end of the elongated housing, wherein the rail wire extends through the rail wire channel, and wherein the laser delivery member is slidably coupled to the rail wire; and
    an actuation mechanism coupled to the elongated housing and the laser delivery member, the actuation mechanism having a body and a plunger disposed at least partially within the body, whereupon distally advancing the plunger advances the laser delivery member along the rail wire, the rail wire being adapted to position the second distal end laterally away from and substantially parallel to the central axis as the second distal end is at or beyond the apex section of the ramp.

2. The catheter of claim 1, wherein the rail wire extends through the ramp but not the nose section.

3. The catheter of claim 1, wherein the nose section is a rounded tip having minimal thickness.

4. The catheter of claim 1, wherein the first distal end includes a first distal edge, the first distal edge defining a line extending therefrom and substantially perpendicular to the central axis, and the second distal end includes a second distal edge, wherein distally advancing the plunger advances the second distal edge to the line.

5. The catheter of claim 1, the elongated housing further comprising a guidewire channel.

6. The catheter of claim 5, wherein the guidewire channel is in communication with the ramp.

7. The catheter of claim 6 further comprising a guidewire exiting through the guidewire channel.

8. The catheter of claim 5, wherein the guidewire channel includes a side port.

9. The catheter of claim 5, the elongated housing further comprising a sheath, wherein the guidewire channel is disposed within the sheath.

10. A catheter system comprising:
    an elongated housing having:
        a first proximal end, a first distal end, a central axis, and a housing channel disposed between the first proximal end and the first distal end, a cavity disposed proximate the first distal end of the elongated housing and in communication with the housing channel;
        the first distal end having:
            a ramp having an inclining proximal section and an apex section;
            a nose section disposed distally of the ramp; and
            a rail wire channel in communication with the ramp;
    a laser delivery member having:
        a second proximal end, a second distal end, at least one optical fiber, and a guidewire channel, the laser delivery member being at least partially disposed within the housing channel and movable therein, the ramp adapted to move the second distal end of the laser delivery member laterally away from the central axis of the elongated housing when the distal end of the laser delivery member is on the ramp;
    a rail wire fixedly attached to and terminating at the first distal end of the elongated housing, wherein the rail wire extends through the rail wire channel, and wherein the laser delivery member is slidably coupled to the rail wire; and
    a guidewire extending through the guidewire channel and exiting the second distal end; and
    a trigger mechanism coupled to the elongated housing and the laser delivery member, the trigger mechanism having a body and a plunger disposed at least partially within the body, whereupon distally advancing the plunger advances the laser delivery member along the rail wire, the rail wire being adapted to position the second distal end laterally away from and substantially parallel to the central axis as the second distal end is at or beyond the apex section of the ramp.

11. The catheter of claim 10, wherein the first distal end includes a first distal edge, the first distal edge defining a line extending therefrom and substantially perpendicular to the central axis, and the second distal end includes a second distal edge, wherein distally advancing the plunger advances the second distal edge to the line.

12. The catheter of claim 10, wherein the rail wire and the guidewire do not enter or exit the nose section.

13. The catheter of claim 10, wherein the nose section is a rounded tip having minimal thickness.

14. A method comprising:
positioning a catheter system within a vessel, wherein the catheter system includes:
  an elongated housing having:
    a first proximal end, a first distal end, a central axis, and a housing channel disposed between the first proximal end and the first distal end, a cavity disposed proximate the first distal end of the elongated housing and in communication with the housing channel;
    the first distal end having:
      a ramp having an inclining proximal section and an apex section;
      a nose section disposed distally of the ramp; and
      a rail wire fixedly attached to and terminating at the ramp or nose section;
  a laser delivery member having:
    a second proximal end, a second distal end, at least one optical fiber, the laser delivery member being at least partially disposed within the housing channel and movable therein, the ramp adapted to move the second distal end of the laser delivery member laterally away from the central axis of the elongated housing when the distal end of the laser delivery member is on the ramp; and
  the rail wire extending through a rail wire channel and slidably connected to the laser delivery member;
actuating the actuation mechanism, the actuation mechanism coupled to the elongated housing and the laser delivery member and including a body and a plunger disposed at least partially within the body, whereupon distally advancing the plunger advances the laser delivery member along the rail wire, the rail wire being adapted to position the second distal end laterally away from and substantially parallel to the central axis as the second distal end is at or beyond the apex section of the ramp; and
activating a laser light source to generate light energy to ablate target material within the vessel.

15. The method of claim 14, the first distal end having a first distal edge, the first distal edge defining a line extending therefrom and substantially perpendicular to the central axis, and the second distal end having a second distal edge, wherein distally advancing the plunger advances the second distal edge to the line.

16. The method of claim 14, wherein the rail wire extends through the ramp but not the nose section.

17. The method of claim 14, wherein the nose section is a rounded tip having minimal thickness.

18. The method of claim 17, wherein positioning the catheter includes the laser delivery member being proximate to the target material, separated only by the minimal thickness of the rounded tip of the nose section.

* * * * *